United States Patent [19]
Lajoie et al.

[11] Patent Number: 6,124,094
[45] Date of Patent: Sep. 26, 2000

[54] ZOOGLOEAL AND HYPHOMICROBIUM SPP. NUCLEIC ACIDS

[75] Inventors: Curtis A. Lajoie, Rockwood; Christine Jo Kelly, Philadelphia; Alice C. Layton, Knoxville; Gary S. Sayler, Blain; Raymond Stapleton, Knoxville, all of Tenn.

[73] Assignee: Eastman Chemical Company, Kingsport, Tenn.

[21] Appl. No.: 08/953,171

[22] Filed: Oct. 17, 1997

[51] Int. Cl.$^7$ ...................................................... C12Q 1/68
[52] U.S. Cl. ...................... 435/6; 536/24.32; 536/24.31; 536/24.33; 935/8; 935/78
[58] Field of Search ............................... 536/24.32, 24.3, 536/24.31, 24.33; 935/8, 78; 435/6

[56] References Cited

U.S. PATENT DOCUMENTS 5,462,855  10/1995  Springer et al. ............................. 435/6

OTHER PUBLICATIONS

Lajoie et al. "Molecular Analysis of Zoogloeal Clusters in Viscous Sludge" Proceedings of the Water Environmental Federation Annual Conference Exposition, vol. 3, 1997, pp. 317–326.

Anders et al. "Taxonomic Position of Aromatic–Degrading Denitrifying Pseudomonad Strains K 172 and KB 740 and Their Description as New Members of the Genra Thauera, as *Thauera aromatica* sp. nov., and Azoarcus, as *Azoarcus evansii* sp. nov., respectively, Members of the Beta Subclass of the Proteobacteria" *Int. J. Sys. Bacteriol.* 327–333, Apr. 1995.

Macy et al. "*Thauera selenatis* gen. Nov., sp. Nov., a Member of the Beta Subclass of proteobacteria with a Novel Type of Anaerobic Respiration" *Int. J. Sys. Bacteriol.*, 135–142, Jan. 1993.

Fesefeldt, A. and Gliesche, C.G. "Identification of Hyphomicrobium spp. using PCR–Amplified Fragments of the mxaF Gene as a Molecular Marker" *System. Appl. Microbiol.* 20:387–396, 1997.

Ming–Chien, S., Cha, Dainel K., and Anderson, P.R. "Influence of Selector Technology on Heavy Metal Removal of Activated Sludge Secondary Effects of Selector Technology" *Wat. Res.* 29(3):971–976, 1995.

Myers, A.J. and Myers, C.D. Hyphomicrobium–mediated Sludge Bulding in an Industrial Wastewatewater Treatment System Abstract 86th Annual Meeting of the Amer. Society for Microbiol. Washington, DC Mar. 23–28, 1986, Abstracts of the Annual Meeting—1986,No. N–93, p. 257.

Rabus et al. Arch. Microbiol. (1995) 163:96–103, Apr. 1995.

Seviour, E.M. et al. (1997) "The filamentous morphotype Eikelboom Type 1863 is not a single genetic entity" *J. Applied Microbiol.* 82:411–421.

Reyes, F.L., Ritter, W., Raskin, L. (1997) Group–specific small–subunit rRNA hybridization probes to characterize filamentous foaming in activated sludge systems. *Applied and Environmental Microbiology* 63(3), 1107–1117.

Holm, N.C., Gliesche, C.G., Hirsch, P. (1996) "Diversity and structure of Hyphomicrobium populations in a sewage treatment plant and its adjacent receiving lake," *Applied and Environmental Microbiology*, 62(2), 522–528.

Amaral, J.A., Archambault, C., Richards, S.R., Knowles, R. (1995) Denitrification associated with Groups I and II methanotrophs in a gradient enrichment system. *FEMS Microbiology Ecology* 18, 289–298.

Rossello–Mora, R., Wagner, M., Amann, R., and Schleiffer, K.–H. (1995) "The abundance of *Zoogloea ramigera* in sewage treatment plants." *Applied and Environmental Microbiology*, vol. 61, No. 2, pp. #702–707.

Wagner, M., Amann, R., Kampfer, P., Assmus, B., Hartman, Hutzler, P., Springer, N., Schleifer, K. (1994) "Identification and in situ detection of gram–negative filamentous bacteria in activated sludge." *Syst. Appl. Microbiol.* 17, 405–417.

Jenkins, David et al. (1993) Manual on the Causes and Control of activated Sludge Bulking and Foaming, 2nd Ed., Lewis Publishers, Chelsea, Michigan.

Shin, Y.K., Hiraishi, A., and Sugiyama, J. (1993) "Molecular systematics of the genus Zoogloea and emendation of the genus." *Int. J. Syst. Bacteriol.*, vol. 43, No. 4, pp. #826–831.

(List continued on next page.)

*Primary Examiner*—Kenneth R. Horlick
*Assistant Examiner*—Janell E. Taylor
*Attorney, Agent, or Firm*—Cheryl J. Tubach; Harry J. Gwinnell

[57] ABSTRACT

The invention provides two new zoogloeal strains, mz1t and mz2t. The invention provides an isolated nucleic acid consisting of the nucleic acid of SEQ ID NO:1. Examples of nucleic acids of mz1t include SEQ ID NO:2 and SEQ ID NO:3. An example of a nucleic acid of mz2t is SEQ ID NO:4. The invention also provides an isolated nucleic acid consisting of the nucleic acid of SEQ ID NO:5. A method of detecting the presence of zoogloeal clusters in a wastewater sample is provided, comprising: a) contacting RNA from a sample of the wastewater with a nucleic acid comprising the nucleic acid of SEQ ID Nos:1,2,3,4 or 5 under conditions that permit specific hybridization; and b) detecting the presence of hybridization, the presence of hybridization indicating the presence of zoogloeal clusters. A new Hyphomicrobium spp. strain, designated M3, is provided herein. The invention provides novel nucleic acids of a Hyphomicrobium sp. M3. For example SEQ ID NO:6 and SEQ ID NO:7 rDNAs of M3. SEQ ID Nos:8, 9, 10, 11, 12, 13 and 14 are presumptive Hyphomicrobium spp. sequences. SEQ ID NO:15 is a consensus sequence from 6m3 and 3m3 (Hyphomicrobium sp. m3 isolated from sludge. A method of detecting the presence of a Hyphomicrobium species in a wastewater sample as described above, using a nucleic acid comprising the nucleic acid of SEQ ID NO:17 is also provided. The nucleic acids of SEQ ID NO:6, SEQ ID NO:7, SEQ ID NO:8, SEQ ID NO:9, SEQ ID NO:10, SEQ ID NO:11, SEQ ID NO:12 SEQ ID NO:13, SEQ ID NO:14 and SEQ ID NO:15 can also be utilized in whole or as fragments in the detection method for Hyphomicrobium spp.

25 Claims, No Drawings

OTHER PUBLICATIONS

Wagner, M., Amann, R., Lemmer,H., Schleifer, K. (1993) "Probing activated sludge with oligonucleotides specific for Proteobacteria: Inadequacy of culture dependent methods for describing microbial community structure." *Applied and Environmental Microbiology* 59(5), 1520–1525.

Unz, R.F. (1984). "Genus IV. Zoogloea Itzigosohn." in *Bergey's Manual of Systematic Bacteriology* (N.R. Krieg and J.G. Holt, eds.), Williams and Wilkins, Baltimore, MD. vol. 1, pp. #214–219.

Unz, R.F. (1971). "Neotype strain of *Zoogloea ramigera* Itzigsohn." *Int. J. Syst. Bacteriol.*, vol. 21, pp. #91–99.

ZOOGLOEAL AND HYPHOMICROBIUM SPP. NUCLEIC ACIDS

BACKGROUND OF THE INVENTION

1. Field of the Invention

The invention relates to methods of detecting bacterial strains associated with sludge problems at wastewater treatment plants. More specifically, the invention relates to the identification of novel bacterial strains associated with sludge problems at wastewater treatment plants. Most specifically, the invention relates to nucleic acid probes for use in detecting bacterial strains associated with sludge problems.

2. Background Art

Two important desired qualities of sludges at wastewater treatment plants are dewaterability and compactability. Microscopic observations at industrial wastewater treatment facilities have demonstrated that the presence of zoogloeal clusters is correlated with episodes of poor sludge dewaterability, and the presence of Hyphomicrobium sp. is associated with poor sludge compaction.

Plant operations designed to enhance endogenous respiration in one of three aeration basins have resulted in significant decreases in sludge yield (Bullard and Barber, 1994). However, periodic episodes of poor sludge dewaterability have limited applications of this sludge minimization strategy (Barber et al., 1995). Microscopy has indicated that decreased dewatering potential is correlated with the presence of amorphous zoogloeal clusters, although these clusters are also commonly present at lesser abundance during periods of good sludge quality.

Identifying and monitoring organisms forming zoogloeal clusters in activated sludge is complicated due to the lack of distinctive morphological or physiological characteristics delineating the genus Zoogloea (Unz, 1984). Historically, identification of species as Zoogloea spp. has been based primarily on the fact that they were isolated from wastewater and formed flocs (Crabtree and McCoy, 1967; Unz, 1971; Friedman and Dugan, 1968). The lack of distinctive conserved characteristics has rendered microscopic observation the only currently available monitoring method.

New developments in molecular based methods for microbial classification and identification, based on the sequence of the RNA found in the small ribosomal subunit (16S rRNA), have made possible a more complete and definitive analysis of complex microbial communities. However, this technology has not been fully utilized in the analysis of sludge microbial communities.

16S rRNA sequence analysis of strains previously classified as Zoogloea spp. has indicated that these organisms are not closely related (Shin et al., 1993). Whereas *Z. ramigera* ATCC 19623 is in the alpha subclass of the Proteobacteria, *Z. ramigera* ATCC 19544 and *Z. ramigera* 25935 are members of the beta subclass. Probing of activated sludge with 16S rRNA probes developed for the three major type strains (Zoogloea spp. ATCC 19623, 19544, and 25935) has suggested that only *Z. ramigera* ATCC 19544 is commonly present as zoogloeal clusters (Rossello-Mora et al., 1995; Wagner et al., 1995). Whether additional species are involved in zoogloea formation and associated dewatering problems has not been determined.

The application of fluorescent probes for in situ detection of Gram-negative filamentous bacteria in activated sludge is relatively new (Bradford et al., 1997, Reyes et al., 1997, Wagner et al., 1993, Wagner et al., 1994). Although, these researchers have developed a variety of oligonucleotide probes for Proteobacteria, 16S rDNA probes for Hyphomicrobium spp. have not been previously reported. Hyphomicrobium spp. have been observed in sewage treatment plants (Holm et al., 1996) and their presence in soils, groundwater, freshwater ponds and lakes, marine samples and hypersaline lakes have also been reported. Previous studies have shown that *Hyphomicrobium vulgare* characteristically grows in clumps, often adhering to the walls of the culture vessel. Hyphomicrobium-like bacterium are commonly present in the natural environment, and utilized methanol under denitrifying conditions (Amaral et al., 1995). Hyphomicrobium spp. are competitive under low nutrient conditions (Bergey's Manual of Determinative Bacteriology).

The present invention provides the identity of organisms comprising zoogloeal clusters in a wastewater treatment plant and 16S rRNA oligonucleotide probes for their routine monitoring. The invention also provides 16S rRNA oligonucleotide probes for the routine monitoring of Hyphomicrobium spp.

SUMMARY OF THE INVENTION

The invention provides two new zoogloeal strains, mz1t and mz2t. These strains can be identified by their novel nucleic acids and other characteristics as further described below.

The invention provides an isolated nucleic acid consisting of the nucleic acid of SEQ ID NO:1. This nucleic acid can be a probe (Rhodo probe), which hybridizes primarily to members of the genera Thauera, Azoarcus, Zoogloea and Rhodocyclus as described in the Examples.

Examples of nucleic acids of mz1t include SEQ ID NO:2 and SEQ ID NO:3, 5'-3' bases 530–1130 and 940–1492, respectively. An example of a nucleic acid of mz2t is SEQ ID NO:4, 5'-3' bases 1080–1492. Numerous strain specific fragments of these nucleic acids can be derived using the sequence comparison methods described herein and routinely in the art.

The invention also provides an isolated nucleic acid consisting of the nucleic acid of SEQ ID NO:5. This probe (MZ1 probe) also targets both strains mz1t and mz2t and an Azoarcus sp. Thus, the MZ1 probe targets members of the genus Thauera which form zoogloeal clusters in the sludges at some wastewater treatment facilities.

A method of detecting the presence of zoogloeal clusters in a wastewater sample is provided, comprising: a) contacting RNA from a sample of the wastewater with a nucleic acid comprising the nucleic acid of SEQ ID NO:1 under conditions that permit specific hybridization; and b) detecting the presence of hybridization, the presence of hybridization indicating the presence of zoogloeal clusters.

A method of detecting the presence of zoogloeal clusters in a wastewater sample, as described above, but using a nucleic acid comprising the nucleic acid of SEQ ID Nos:2, 3,4 or 5 is also provided.

A new Hyphomicrobium spp. strain, designated M3, is provided herein. These strains can be identified by their novel nucleic acids and other characteristics as further described below.

The invention provides novel nucleic acids of a Hyphomicrobium sp. M3.

For example SEQ ID NO:6 and SEQ ID NO:7 are 5'-3' bases 30–1490 rDNAs of M3, replicate 1 (6M3) and replicate 2 (3M3), respectively. SEQ ID Nos:8, 9, 10, 11, 12, 13 and 14 are presumptive Hyphomicrobium spp. sequences derived from sludge (7 partial sequences~1060–1492). SEQ ID NO:15 is a consensus sequence from 6M3 and 3M3 (Hyphomicrobium sp. M3 isolated from sludge.

A method of detecting the presence of a Hyphomicrobium species in a wastewater sample is provided. The method comprises a) contacting DNA from a sample of the wastewater with a nucleic acid comprising the nucleic acid of SEQ ID NO:16 under conditions that permit specific hybridization; and b) detecting the presence of hybridization, the presence of hybridization indicating the presence of a Hyphomicrobium species.

A method of detecting the presence of a Hyphomicrobium species in a wastewater sample as described above, but using a nucleic acid comprising the nucleic acid of SEQ ID NO:17 is also provided. The nucleic acids of SEQ ID NO:6, SEQ ID NO:7, SEQ ID NO:8, SEQ ID NO:9, SEQ ID NO:10, SEQ ID NO:11, SEQ ID NO:12 SEQ ID NO:13, SEQ ID NO:14 and SEQ ID NO:15 can also be utilized in whole or as fragments in the detection method for Hyphomicrobium spp.

DETAILED DESCRIPTION OF THE INVENTION

Novel zoogloeal strains

The invention provides two new zoogloeal strains, mz1t and mz2t. These strains can be identified by their novel nucleic acids and other characteristics as further described below.

The term "zoogloea" refers to the organisms found in clusters of cells in biological sludge, and the clusters themselves are referred to as "zoogloeal clusters." When the taxonomic identity of the organisms forming the clusters are unknown the organisms are referred to as "zoogloeal strains."

Workers in the field of wastewater treatment often use the term "zoogloea" to describe the groups of organisms that grow as clusters interspersed with polysaccharides such that the individual cells are distinctly visible. Whether the organisms forming these clusters are members of the genus Zoogloea is largely unknown, although probing with the *Z. ramigera* ATCC 19544 targeted probe (ZRA), developed by other researchers, indicate that some clusters are formed by this organism. The present results demonstrate that the clusters observed in the activated sludge of at least one wastewater treatment facility do not probe positive with this probe, but two new zoogloeal strains have been identified (mz1t and mz2t). Strains mz1t and mz2t are most closely related to known members of the genus Thauera as further described in the Examples.

Zoogloeal strain nucleic acids

The invention provides an isolated nucleic acid consisting of the nucleic acid of SEQ ID NO:1. This nucleic acid can be a probe (Rhodo probe), which hybridizes primarily to members of the genera Thauera, Azoarcus, Zoogloea and Rhodocyclus as described in the Examples. The Rhodo probe targets both *Z. ramigera* ATCC 19544 and two new zoogloeal strains, mz1t and mz2t. Thus, it can be used as a probe to group zoogloea.

An isolated nucleic acid comprising the nucleic acid of SEQ ID NO:1 is also within the invention. Nucleotides can be added to either the 5' or 3' end of SEQ ID NO:1 and the resulting nucleic acid tested for its ability to detect at least one of the group of organisms with which the Rhodo probe hybridizes. The Rhodo probe targets a broader range of organisms than the MZ1 probe (described below). Adding bases to the Rhodo probe would be expected to increase its specificity, and thereby, eliminate some target strains or include non-target strains depending on whether the added bases are conserved or divergent, or whether hybridization formamide concentration or temperature is increased or decreased, as specificity is effected both by the number of mismatches between the probe and the targeted nucleic acid and the temperature and formamide concentration.

The invention provides novel nucleic acids of mz1t. Thus, the invention provides a nucleic acid specific for the bacterial strain designated mz1t or a nucleic acid complementary thereto. These nucleic acids can encode mz1t proteins or they can be rDNA or rRNA (e.g., 16S rRNA), or they can be complementary to nucleic acids of mz1t or mz2t (e.g., probes or primers). The invention also provides other non-complementary nucleic acids that specifically hybridize with nucleic acids specific for mz1t. A nucleic acid that specifically hybridizes with a mz1t-specific region of the nucleic acid of the nucleic acid of an mz1t-specific nucleic acid is also provided.

Examples of nucleic acids of mz1t include SEQ ID NO:2 and SEQ ID NO:3, 5'-3' bases 530–1130 and 940–1492, respectively. Numerous strain specific fragments of these nucleic acids can be derived using the sequence comparison methods described herein and routinely in the art.

The invention provides novel nucleic acids of mz2t. Thus, the invention provides a nucleic acid specific for the bacterial strain designated mz2t or a nucleic acid complementary thereto. These nucleic acids can encode mz2t proteins or they can be rDNA or rRNA (e.g., 16S rRNA), or they can be complementary to nucleic acids of mz1t or mz2t (e.g., probes or primers). The invention also provides other non-complementary nucleic acids that specifically hybridize with nucleic acids specific for mz2t. A nucleic acid that specifically hybridizes with a mz1t-specific region of the nucleic acid of the nucleic acid of an mz2t-specific nucleic acid is also provided. An example of a nucleic acid of mz2t is SEQ ID NO:4, 5'-3' bases 1080–1492. Numerous strain specific fragments of these nucleic acids can be derived using the sequence comparison methods described herein and routinely in the art.

The invention also provides an isolated nucleic acid consisting of the nucleic acid of SEQ ID NO:5. This probe (MZ1 probe) also targets both strains mz1t and mz2t and an Azoarcus sp. Thus, the MZ1 probe targets members of the genus Thauera which form zoogloeal clusters in the sludges at some wastewater treatment facilities.

An isolated nucleic acid comprising the nucleic acid of SEQ ID NO:5 is also within the present invention. Nucleotides can be added to either the 5' or 3' end of SEQ ID NO:5 and the resulting nucleic acid tested for its ability to detect at least one of group of organisms with which the MZ1 probe hybridizes. If it is desired to detect both mz1t and mz2t, bases can be added (up to 1500 bases) as long as the mz1t and mz2t rRNA sequences do not diverge within the sequence used as the probe. At the point of divergence, the probe would become more specific for either mz1t or mz2t.

The Examples more clearly define the target range in terms of the genera to which the present probes are complementary. Research on 16S rRNA sequences of the three major type strains previously classified as *Zoogloea ramigera*, performed by other researchers, indicated that the these species are not closely related. Only one of these (*Z. ramigera* ATCC 19544) is expected to remain in the genus Zoogloea as the type strain. The other two strains are expected to be moved to other as yet undetermined genera.

The zoogloea nucleic acid probes of this invention can be a nucleic acid comprising the nucleotide sequence of a coding strand or its complementary strand or the nucleotide sequence of a sense strand or antisense strand. Thus, the probe of this invention can be either DNA or RNA and can bind either DNA or RNA in the biological sample. The nucleotide sequence of the probe can be any sequence having sufficient complementarity to a nucleic acid sequence in the sludge sample to allow for hybridization of the probe to the target nucleic acid(s) in the biological sample under various hybridization conditions. Ideally, the probe will hybridize only to the nucleic acid target(s) of interest in the sample and will not hybridize non-specifically to non-target nucleic acids in the sample. The hybridization conditions can be varied according to the degree of stringency desired in the particular hybridization protocol (e.g., in situ, solution hybridization, blots etc.). For example, if the hybridization conditions are for high stringency, which employs high temperature and low salt conditions, the probe will bind only to the nucleic acid sequences in the sample with which it has a very high degree of complementarity. Low stringency hybridization conditions, employing low temperature and high salt, allow for hybridization of the probe to nucleic acid sequences in the sample which have some complementarity but which are not as highly complementary to the probe sequence as would be required for hybridization to occur at high stringency. The hybridization conditions will vary depending on the biological sample, probe type and target (s). An artisan will know how to optimize hybridization conditions for a particular application of the present nucleic acids. Examples of hybridization conditions are described in the Examples provided herein.

The probes have been designed to achieve a desired specificity. If the region adjacent to the probe target is a conserved region, adding bases will tend to decrease probe specificity, i.e. the proportion of bases conferring discrimination is decreased. While it can still be possible to achieve discrimination, it becomes hard to achieve selectivity with a greater proportion of bases that do not provide discrimination. Also, as the length increases the probe is less likely to enter permeabilized cells in in situ hybridization experiments. If the adjacent region is very variable, then an increase in probe length renders it more specific. In this case, the "grouping function" of the probe is compromised, and some desired target sequences may not hybridize. In the preferred case, the nucleic acids comprising the presently disclosed oligonucleotides are expected to range from about 16 to 22 nucleotides in length.

Target sequences are the sequences identified in the 16S rDNA of naturally occurring bacteria by DNA sequencing. Relationships between organisms are determined by grouping target sequences together based on their similarity. Oligonucleotide probe sequences are deduced sequences based on analyzing the relationships between the target sequences. The oligonucleotide probe is made by first complementing the base pairs found in a single or a group of target sequences and then reversing the order of the bases from 3'–5' to 5'–3' for synthesis. The relationship between the target sequences and the oligonucleotide probes are shown in Table 1. When designing nucleotide probes, the finding of identical stretches in target sequences of relevant bacterial isolates is crucial. The addition, subtraction or changing of a single base in the oligonucleotides probe is likely to change the range of organisms detected by the probe.

TABLE 1

The target sequences and deduced oligonucleotide probes for this patent application.

|  | Organism(s) detected | Target sequence 5'-3' (position in 16S rDNA) | Oligonucleotide Probe 5'-3' |
|---|---|---|---|
| MZ1 | Mzt, Thauera sp. | AAGGCTAGAGTACGGC | TCTGCCGTACTCTAGCC |
| Rhodo | Mzt, Thaurea spp., Z. ramigera ATCC 19544, Azoarcus spp., Rhodocyclus spp. | GCCGATCGTAGTCCGGAT | ATCCGGACTACGATCGGC (SEQ ID NO:1) |
| Hypho C | Hyphomicrobium spp. | GGCGGTGACAATGGGCAGC | GCTGCCCATTGTCACCGCC |
| Hypho G | Hyphomicrobium sp. | GGCGGTGACAATGCGCAGC | GCTGCGCATTGTCACCGCC |

Oligonucleotide Probe = the reverse of the compliment to the garget sequence.

The invention provides an isolated nucleic acid that selectively or specifically hybridize with the sequence set forth as SEQ ID NO:1, SEQ ID NO:2, SEQ ID NO:3, SEQ ID NO:4 or SEQ ID NO:5 under the hybridization conditions described herein. For example, the hybridizing nucleic acid can be a probe that hybridizes to the RNA of one or more of the exemplified strains. The hybridizing nucleic acid can also include insubstantial base substitutions that do not prevent hybridization under the stated conditions.

As used herein to describe a nucleic acid sequence (oligonucleotide, RNA, DNA, probe, primer etc.), "specific" means that the nucleic acid is not found identically in any other source. The determination of specificity is made routine, because of the availability of computerized sequence databases, wherein a nucleic acid sequence of almost any length can be quickly and reliably checked for the existence of identical sequences. If an identical sequence is not found, the nucleic acid is "specific" for the recited source. A nucleic acid can be rDNA/rRNA specific (i.e., found in rDNA/rRNA from any source, but not in other genes), group-specific (e.g., found in the rRNA/rDNA of related genera, but not in unrelated groups), genus-specific (e.g., found in the rRNA/rDNA of multiple species of the genus Hyphomicrobium, but not in any other genera), species-specific (e.g., found in the rRNA/rDNA of a particular Hyphomicrobium species, but not in any other species), or strain-specific (i.e., found in a particular zoogloeal strain, but not in an rRNA or rDNA of a different zoogloeal strain). If the rRNA/rDNA sequence is highly conserved it may be found on many otherwise unrelated sources.

As used herein to describe nucleic acids, the term "selectively hybridizes" excludes the occasional randomly hybridizing nucleic acids, and further distinguishes what is recognized in the art as background hybridization. As used herein "specific" hybridization means the nucleic acid hybridizes only to the reference nucleic acid at high stringency. The hybridizing nucleic acids of the invention can have at least 90%, 91%, 92%, 93%, 94%, 95%, 96%, 97%, 98% 99%, and 100% complementarity with the segment and strand of the sequence to which it hybridizes. The nucleic acids used as probes are typically 18, 19, 20, 21, or 22 nucleotides in length. However, depending on whether the nucleic acid is to be used as a primer or for other purposes, it can be longer or shorter. Typically, 16S rRNA probes are kept in the range of 20 bases as longer probes are not as effective for in-situ (whole cell) hybridization as they cannot as readily enter permeabilized cells. If used as primers, the invention provides compositions including at least two nucleic acids which selectively hybridize with different regions so as to amplify a desired region. Depending on the length of the probe or primer, it can range between 90% complementary bases and full complementarity and still hybridize under stringent conditions. For example, for the purpose of detecting the presence of zoogloeal strains, the degree of complementarity between the hybridizing nucleic acid (probe or primer) and the sequence to which it hybridizes (DNA or RNA from a sample) should be at least enough to exclude hybridization with a nucleic acid from unrelated bacteria. The invention provides examples of these nucleic acids, so that the degree of complementarity required to distinguish selectively hybridizing from nonselectively hybridizing nucleic acids under stringent conditions can be clearly determined for each nucleic acid.

"Stringent conditions" refers to the washing conditions used in a hybridization protocol. The temperature and salt conditions needed to attain a specified level of stringency are readily determined empirically in experiments in which samples of reference RNA immobilized on filters or permeabilized whole cells immobilized on glass slides are hybridized to the probe of interest and then washed under conditions of different stringencies. Examples of stringent conditions are described below.

Detecting zoogloea strains

Zoogloeal clusters can be involved in poor sludge compaction and dewatering during plant start-up, and are involved in episodes of viscous bulking. However, they are also commonly observed in treatment systems employing selectors, and are not necessarily associated with sludge quality problems. It is possible that comparative probing in different wastewater treatment plants will indicate that some zoogloeal stains tend to be more problematic than others. Improved monitoring methods may result in more specific diagnosis of activated sludge process performance problems, and allow more flexibility in process control strategies.

A method of detecting the presence of zoogloeal clusters in a wastewater sample is provided, comprising: a) contacting RNA from a sample of the wastewater with a nucleic acid comprising the nucleic acid of SEQ ID NO:1 under conditions that permit specific hybridization; and b) detecting the presence of hybridization, the presence of hybridization indicating the presence of zoogloeal clusters.

A method of detecting the presence of zoogloeal clusters in a wastewater sample, as described above, but using a nucleic acid comprising the nucleic acid of SEQ ID NO:5 is also provided.

Because of the target specificity of SEQ ID NO:5, a method of detecting the presence of the Thauera spp. isolate mz1t or mz2t in a wastewater sample is provided. The method comprises the steps of a) contacting RNA from a sample of the wastewater with a nucleic acid comprising the nucleic acid of SEQ ID NO:5; under conditions that permit specific hybridization; and b) detecting the presence of hybridization, the presence of hybridization indicating the presence of the Thauera sp. isolate mz1t or mz2t.

Because certain of the bacteria detected using the Rhodo probe are associated with sludge dewatering problems, a method of detecting bacteria in sludge that are associated with sludge dewatering problems is provided. The method comprises a) contacting DNA from the bacteria with a nucleic acid comprising the nucleic acid of SEQ ID NO:1 under conditions that permit specific hybridization; and b) detecting the presence of hybridization, the presence of hybridization indicating the presence of a bacterium associated with sludge dewatering problems.

Because certain bacteria detected by the MZ1 probe are associated with sludge dewatering problems, the method of detecting bacteria in sludge that are associated with sludge dewatering problems as described above, but using a nucleic acid comprising the nucleic acid of SEQ ID NO:5 is also provided.

The invention also provides a method of detecting bacteria in sludge that are associated with sludge dewatering problems, comprising: a) contacting DNA from the bacteria with the nucleic acid of SEQ ID NO:1 and the nucleic acid of SEQ ID NO:5 under conditions that permit specific hybridization; and b) detecting the presence of hybridization, the presence of hybridization indicating the presence of a bacterium associated with sludge dewatering problems.

The above described methods can use the nucleic acids of SEQ ID NO:2, SEQ ID NO:3 and SEQ ID NO:4 to detect the presence of zoogloea and other certain other bacteria associated with sludge dewatering problems.

The conditions, which can be used for the fluorescent probing and dot blot hybridization described herein are described in the Examples. The experimentally determined formamide concentration for single mismatch discrimination between probe and target for both the Rhodo and MZ1 probes is 40%. There can be some variability in this depending on salt concentration in the specific hybridization solution. As indicated in the Examples it is not always desirable to run the hybridization at the highest stringency. It depends on what the primary goal is. For example, in some cases signal strength is more important than specificity. More specifically, there may be Thauera spp. with minor (1 base) sequence differences that have not yet been identified. Generally, the question of stringency relates to the argument of signal intensity. This is the more common issue. Stringency needed to achieve one mismatch discrimination can result in a weaker signal for the target strain. It is often desirable to have a strong easily detectable signal, and the slight loss of specificity is not a problem.

The dot blot hybridization follows standard protocols referenced in the Examples. The temperature condition determined for single mismatch discrimination is somewhere between 60 and 65° C. The prime controller of specificity in in situ (whole cell) hybridization is formamide concentration, whereas the controlling factor in dot blot hybridizations is temperature.

Zoogloeal clusters can cause dewatering problems, but do not always cause problems. Whether problems are related to different species forming clusters, the total amount of clusters, or the level of expression of polysaccharide synthesis is not known. Zoogloeas can form clusters (amorphous form) or finger-like projections. In either case, the distinguishing characteristic is that individual cells are readily visible in a gelatinous matrix. In typical sludge flocs the individual cells are difficult to see, and the matrix is more opaque. Both types of zoogloeas (amorphous and finger-like can cause dewatering problems). Dewatering problems can also be associated with nitrogen or phosphorus deficiency in the incoming wastewater. In this case, zoogloeal clusters or fingers may be absent.

Novel Hyphomicrobium species

A new Hyphomicrobium spp. strain, designated M3, is provided herein. These strains can be identified by their novel nucleic acids and other characteristics as further described below.

Hyphomicrobium spp. nucleic acids

The invention provides novel nucleic acids of a Hyphomicrobium sp. M3. Also provided is a nucleic acid specific for the bacterial strain designated M3 or a nucleic acid complementary thereto. These nucleic acids can encode M3 proteins or they can be rDNA or rRNA (e.g., 16S rRNA), or they can be complementary to nucleic acids of M3 (e.g., probes or primers). A nucleic acid that specifically hybridizes with a M3-specific region of the nucleic acid of the nucleic acid of a M3-specific nucleic acid is also provided.

For example SEQ ID NO:6 and SEQ ID NO:7 are 5'–3' bases 30–1490 rDNAs of M3, replicate 1 (6M3) and replicate 2 (3M3), respectively. SEQ ID Nos:8, 9, 10, 11, 12, 13 and 14 are presumptive Hyphomicrobium spp. sequences derived from sludge (7 partial sequences~1060–1492. SEQ ID NO:15 is a consensus sequence from 6M3 and 3M3 (Hyphomicrobium sp. M3 isolated from sludge. The invention also provides other non-complementary nucleic acids that specifically hybridize with nucleic acids specific for M3.

An isolated nucleic acid consisting of the nucleic acid of SEQ ID NO:16 is provided. An isolated nucleic acid consisting of the nucleic acid of SEQ ID NO:17 is also provided. These nucleic acids provide a degenerate Hyphomicrobium spp. probe—5'-GCTGC(C/G)CATTGTCACCGCC-3'. This is actually two probes: SEQ ID NO:16— GCTGCCCATTGTCACCGCC; and SEQ ID NO:17— GCTGCGCATTGTCACCGCC. A bacterial sample can be probed with both probes in cases where the target organisms have some variability at one or more base locations in the target region. Alternatively, a base analog can be used in place of C or G to minimize the effect of variability at this location. Another alternative strategy is to lower the stringency if one probe is used to achieve the same effect. This probe was designed to include *Hyphomicrobium vulgaris* and H. str. Hyp353 (Illinois 16S rRNA activated sludge database), the Hyphomicrobium sp. isolated from a treatment plant, and Hyphomicrobium-like RNA sequences derived from 16S rDNA sequences obtained by direct amplification of 16S rRNA from DNA extracted from sludge at the same treatment plant. The database Hyphomicrobium spp. would be targeted more specifically by using only a (C) in the degenerate position. Certain other Hyphomicrobium sp. isolates and sludge sequences would more specifically be targeted by using a (G) in the same position. Thus, the nucleic acids of SEQ ID NO:16 and SEQ ID NO:17 specifically hybridize to a nucleic acid of the genus Hyphomicrobium.

An isolated nucleic acid comprising the nucleic acid of SEQ ID NO:16 is also provided. Nucleotides can be added to either the 5' or 3' end of SEQ ID NO:16 and the resulting nucleic acid tested for its ability to detect at least one of a group of organisms with which the SEQ ID NO:16 probe specifically hybridizes.

An isolated nucleic acid comprising the nucleic acid of SEQ ID NO:17 is also provided. Nucleotides can be added to either the 5' or 3' end of SEQ ID NO:17 and the resulting nucleic acid tested for its ability to detect at least one of a group of organisms with which the SEQ ID NO:17 probe specifically hybridizes.

The Hyphomicrobium nucleic acids and probes of the present invention can be a nucleic acid comprising the nucleotide sequence of a coding strand or its complementary strand or the nucleotide sequence of a sense strand or antisense strand. Thus, the probe of this invention can be either DNA or RNA and can bind either DNA or RNA in the biological sample. The nucleotide sequence of the probe can be any sequence having sufficient complementarity to a nucleic acid sequence in the sludge sample to allow for hybridization of the probe to the target nucleic acid(s) in the biological sample under various hybridization conditions. Ideally, the probe will hybridize only to the nucleic acid target(s) of interest in the sample and will not hybridize non-specifically to non-target nucleic acids in the sample. The hybridization conditions can be varied according to the degree of stringency desired in the particular hybridization protocol (e.g., in situ, solution hybridization, blots etc.). For example, if the hybridization conditions are for high stringency, which employs high temperature and low salt conditions, the probe will bind only to the nucleic acid sequences in the sample with which it has a very high degree of complementarity. Low stringency hybridization conditions, employing low temperature and high salt, allow for hybridization of the probe to nucleic acid sequences in the sample which have some complementarity but which are not as highly complementary to the probe sequence as would be required for hybridization to occur at high stringency. The hybridization conditions will vary depending on the biological sample, probe type and target(s). An artisan will know how to optimize hybridization conditions for a particular application of the present nucleic acids. Examples of hybridization conditions are described in the Examples provided herein.

The probes have been designed to achieve a desired specificity. If the region adjacent to the probe target(s) is a conserved region, adding bases will tend to decrease probe specificity, i.e. the proportion of bases conferring discrimination are decreased. It may be still possible to achieve discrimination, but it becomes hard to achieve selectivity with a greater proportion of bases that do not provide discrimination. Also, as the length increases the probe is less likely to enter permeabilized cells in in situ hybridization experiments. If the adjacent region is very variable, then an increase in probe length renders it more specific. In this case, the "grouping function" of the probe is compromised, and some desired target sequences may not hybridize. In the preferred case, the nucleic acids comprising the presently disclosed oligonucleotides are expected to range from about 16 to 22 nucleotides in length.

The invention provides an isolated nucleic acid that selectively or specifically hybridizes with the sequence set forth as SEQ ID NO:6, SEQ ID NO:7, SEQ ID NO:8, SEQ ID NO:9, SEQ ID NO:10, SEQ ID NO:11, SEQ ID NO:12 SEQ ID NO:13, SEQ ID NO:14, SEQ ID NO:15, SEQ ID NO:16 or SEQ ID NO:17, under the hybridization conditions described herein. For example, the hybridizing nucleic acid can be a probe that hybridizes to the RNA of one or more of the exemplified strains. The hybridizing nucleic acid can also include insubstantial base substitutions that do not prevent hybridization under the stated conditions.

As used herein to describe nucleic acids, the term "selectively hybridizes" excludes the occasional randomly hybridizing nucleic acids. It also excludes what would be recognized in the art as background hybridization. As used herein "specific" hybridization means the nucleic acid hybridizes only to the reference nucleic acid at high stringency. The hybridizing nucleic acids of the invention can have at least 90%, 91%, 92%, 93%, 94%, 95%, 96%, 97%, 98%, 99%, and 100% complementarity with the segment and strand of the sequence to which it hybridizes. The nucleic acids used as probes are typically 18, 19, 20, 21, or 22 nucleotides in length. However, depending on whether the nucleic acid is to be used as a primer or for other purposes, it can be longer or shorter. Typically, 16S rRNA probes are kept in the range of 20 bases as longer probes are not as effective for in-situ (whole cell) hybridization as they cannot as readily enter permeabilized cells. If used as primers, the invention provides compositions including at least two nucleic acids which selectively hybridize with different regions so as to amplify a desired region. Depending on the length of the probe or primer, it can range between 90% complementary bases and full complementarity and still hybridize under stringent conditions. For example, for the purpose of detecting the presence of Hyphomicrobium spp., the degree of complementarity between the hybridizing nucleic acid (probe or primer) and the sequence to which it hybridizes (DNA or RNA from a sample) should be at least enough to exclude hybridization with a nucleic acid from unrelated bacteria. The invention provides examples of these nucleic acids, so that the degree of complementarity required to distinguish selectively hybridizing from nonselectively hybridizing nucleic acids under stringent conditions can be clearly determined for each nucleic acid.

"Stringent conditions" refers to the washing conditions used in a hybridization protocol. The temperature and salt conditions needed to attain a specified level of stringency are readily determined empirically in experiments in which samples of reference DNA or RNA immobilized on filters are hybridized to the probe or 16 rRNA coding nucleic acid of interest and then washed under conditions of different stringencies.

Methods of detecting Hyphomicrobium spp.

A method of detecting the presence of a Hyphomicrobium species in a wastewater sample is provided. The method comprises a) contacting DNA from a sample of the wastewater with a nucleic acid comprising the nucleic acid of SEQ ID NO:16 under conditions that permit specific hybridization; and b) detecting the presence of hybridization, the presence of hybridization indicating the presence of a Hyphomicrobium species.

A method of detecting the presence of a Hyphomicrobium species in a wastewater sample as described above, but using a nucleic acid comprising the nucleic acid of SEQ ID NO:17 is also provided. The nucleic acids of SEQ ID NO:6, SEQ ID NO:7, SEQ ID NO:8, SEQ ID NO:9, SEQ ID NO:10, SEQ ID NO:11, SEQ ID NO:12 SEQ ID NO:13, SEQ ID NO:14 and SEQ ID NO:15 can also be utilized in whole or as fragments in the detection method for Hyphomicrobium spp.

Hybridization conditions using the Hyphomicrobium spp. probe of the present invention are provided in the Examples. The temperature for specific dot blot hybridization is 55° C. The formamide concentration for specific in situ hybridization is 45%.

Because Hyphomicrobium spp. are associated with sludge compaction problems, a method of detecting bacteria in sludge that are associated with sludge compaction problems is provided. The method comprises a) contacting DNA from the bacteria with nucleic acid comprising the nucleic acid of SEQ ID NO:3 under conditions that permit specific hybridization; and b) detecting the presence of hybridization, the presence of hybridization indicating the presence of a bacterium associated with sludge compaction problems.

A method of detecting bacteria in sludge that are associated with sludge compaction problems as described above, but using a nucleic acid comprising the nucleic acid of SEQ ID NO:77 is also provided.

Hyphomicrobium spp. are associated with problems with compaction of sludge in the clarifier as the filaments (Hyphomicrobium spp. grow as filaments rather than as clusters) extending from the main body of the sludge flocs hold the sludge flocs apart. This is called filamentous bulking (also caused by other organisms in sludge), and results in the clarifier (settling basin) filling up with a thin, bulky sludge. If unrectified the sludge blanket (at the bottom of the clarifier) can eventually extend to the top of the clarifier, and the sludge overflows from the top and enters the receiving waters (the local river) where the effluent is being discharged.

Maintaining a balance of zoogloea and Hyphomicrobium

Typically, the problems caused by zoogloeal clusters and Hyphomicrobium occur independently. However, in certain cases, these two populations appear to represent two extreme conditions, and process control decisions should be geared to finding a middle ground. The appropriate plant process control responses to both types of strains are known, so monitoring with probes to both is a beneficial. It should also be possible to use probes to both strains in the same hybridization mixture, particularly of different markers are used on the different probes.

EXAMPLE 1

Molecular Analysis of Zoogloeal Clusters in Viscous Sludge

Summary

Probing with 16S rRNA oligonucleotide probes (ZRA and ZBE) indicated that the microorganisms forming zoogloeal clusters in certain treatment plants are not the same as previously classified *Zoogloea ramigera* strains (members of the beta subclass of the Proteobacteria) isolated from other wastewater treatment systems.

The microorganisms responsible for zoogloeal cluster formation were identified using micromanipulator separation, cultivation, and 16S rRNA analysis. Distance matrix tree analysis of isolated strains revealed the presence of two types of microorganisms, referred to as mzt and mzL strains. The mzt isolates grouped most closely with members of the genus Thauera. The mzL isolates grouped more closely with members of the genus Brachymonas. Using a nested probe approach, two 16S rRNA probes were designed. The probe MZ1 targets the mzt strains, and is complementary to members of the genus Thauera. The probe Rhodo is a broader specificity probe designed to target species ranging from the mzt isolates to the *Z. ramigera* type strain ATCC 19544, and is complementary to members of the genera Thauera, Zoogloea, Azoarcus and Rhodocyclus. Whole cell hybridization using fluorescein labeled 16S rRNA probes and epifluorescence microscopy indicated that both of these probes hybridized with the zoogloeal clusters present in the wastewater biosolids.

Wastewater treatment plant characteristics

Activated sludge mixed liquor was obtained from a chemical company wastewater treatment facility. The influent wastewater organic substrates consist primarily of short chain alcohols and low molecular weight organic acids. The plant includes three separate aeration basins in series, and is operated in a modified step feed flow configuration. Typical influent flow splits between the 1st, 2nd, and 3rd aeration basin are 0/80/20 or 50/30/20 percent, respectively (Bullard and Barber, 1994). Samples were taken from a continuous sampling loop, accessible by a sampling valve in an treatment plant laboratory, which continually cycles mixed liquor suspended solids (MLSS, i.e., Biomass) from the third aeration basin.

Isolation and cultivation of zoogloeal clusters

Zoogloeal clusters were separated from activated sludge obtained from a wastewater treatment facility using a micromanipulator (Narishige Model MN-151, Tokyo) mounted on an Olympus inverted microscope (Tokyo). Activated sludge was diluted on a sterile glass microscope slide by placing 1 drop of sludge in 1 drop of sterile synthetic wastewater medium (EASM) containing the same basal inorganic components as the plant influent wastewater. The medium contains the following in mg/L: $CaSO_4.2H_2O$, 740; $Na_2SO_4$, 320; NaCl, 80; $MgSO_4.7H_2O$, 100; 3-N-morpholine-propane sulfonic acid (MOPS), 50; $KH_2PO_4$, 4; $K_2HPO_4$, 14; FeEDTA, 13; $(NH_4)_2SO_4$, 220; $MnSO_4.H_2O$, 10; $Na_2EDTA$, 025; $Na_2MoO_4.2H_2O$, 0.05; $CoCl_2.6H_2O$, 0.001; $ZnSO_4.7H_2O$, 0.05; $CuSO_4.5H_2O$, 0.01.

Individual zoogloeal clusters were drawn into a glass micropipet, the outside of the pipet washed with 95% ethanol, and the cluster ejected into a fresh drop of sterile synthetic wastewater. The micropipet was then rinsed with 95% ethanol and sterile distilled water before drawing the cluster back into the micropipet. The separation procedure was repeated a total three times before ejecting the cluster into an eppendorf tube containing EASM liquid medium. A total of 7 zoogloeal clusters were isolated. The eppendorf tubes containing the zoogloeal clusters were incubated at room temperature until the appearance of visible turbidity. The cultures were streaked to R2A agar plates (Americal Public Health Association, 1989. Standard Methods for Examination of Water and Wastewater 17th Edition, Clesceri, L. S., A. E. Greenberg, and R. Rhodes Trussell (eds.) Washington, D.C.) augmented with simple organic acids and alcohols (R2A/S medium), and individual colony types restreaked for purity before 16S rDNA analysis.

Phylogenetic analysis and probe design

Individual colonies on agar plates were aseptically transferred using an inoculating loop to eppendorf tubes for polymerase chain reaction (PCR) amplification of 16S rDNA. Amplification was performed using the Perkin Elmer GeneAmp PCR reagent kit with AmpliTaq DNA polymerase and the primers 27f and 1492r (Lane, 1991). PCR samples containing buffer, nucleotide primers, and single bacterial colonies were heated to 100° C. for 5 minutes to DNA polymerase was added and PCR amplification was performed for 30 cycles using the following protocol: 94° C. for 1 minute, 45° C. for 1 minute and 72° C. for 1 minute. Final extension to insure full length PCR products was performed at 72° C. for 10 minutes. Successful amplification was verified by agarose gel electrophoresis indicating the presence of a 1.5 kb band.

The amplified 16S rDNA was cloned using the TA Cloning System (Invitrogen Corporation, San Diego, Calif.) following manufacturers' protocols. White colonies were grown in LB medium containing ampicillin or kanamycin, and plasmids were extracted using the basic alkaline lysis procedure as described in the Promega Technical Bulletin 0.009 (Promega, Madison, Wis.). DNA extracts were RNase treated, extracted with an equal volume of chloroform, and precipitated with isopropanol. The pellets were washed with 70% ethanol and dried. Plasmid inserts were verified by EcoRI digestion and gel electrophoresis.

The 16S rDNA was sequenced from purified TA cloning vectors containing full length inserts. Approximately 400 base pairs were sequenced in the 16S rDNA region 1100–1492 using the primer sequence 1492r and single primer extension. Additional sequences were determined in the region 500–900 using the primer sequence 530f or 907r (Lane, 1991). Sequencing was performed by Retrogen, Inc. (San Diego, Calif.) and the Molecular Biology Resource Facility at the University of Tennessee (Knoxville, Tenn.).

Sequences of micromanipulator isolates were compared to other 16S rRNA sequences in the Illinois 16S Ribosomal Data Base Project (RDP) using the program Similarity Rank (Maidak et al., 1994) and to sequences in NCB1 GenBank using the BlastN program (Altshul et al., 1990). Distance matrix trees were constructed using GCG analysis programs to determine relatedness of the activated sludge isolates to each other, to closely related strains as indicated by Similarity Rank analysis, and to 16S rDNA sequences from previously described activated sludge zoogloeal strains.

Probes were designed by visual comparison of 16S rRNA sequences of micromanipulator isolates and known zoogloeal strains. Probe sequences were designed using a nested probe approach to either distinguish between or group micromanipulator isolates from the activated sludge from a wastewater treatment plant and previously reported zoogloeal strains. Probe sequences were analyzed using the program Probe Check to determine if the chosen sequences targeted other known microorganisms for which 16S rRNA sequences are available.

For whole cell hybridization experiments oligonucleotide probes were synthesized using a DNA synthesizer, 5' end-labeled with fluorescein, and purified by reverse phase HPLC (Genosys, The Woodlands, Tex.). The probes were resuspended in TE buffer before use, and stored at −20° C. For slot blot hybridization experiments the oligonucleotides were labeled at their 5' ends using T4 polynucleotide kinase (Life Technologies, Gaithersburg, Md.) and [gamma-$^{32}$P] dATP. The labeled probes were purified using a Stratagene (La Jolla, Calif.) Nuctrap push column.

16S rRNA probing

The procedure for whole cell hybridization experiments using fluorescent 16S rRNA probes was modified from the method of Amann et al. (1990a, b) by the substitution of Igepal CA-630 for Nonidet P-40, and the addition of a 5 minute sonication step in an ice water bath following fixation in paraformaldehyde. Sludge samples were resuspended in 10 mM EDTA prior to sonication to enhance the permeability of the flocs to probe penetration. After hybridization with the fluorescein labeled probes, samples were examined using a Nikon optiphot microscope fitted for epifluorescence with a high pressure mercury bulb and filter set and a Nikon FX-35A camera. Nucleic acid extractions, immobilization on nylon membranes, and dot blot hybridizations were performed according the methods of Hertel et al. (1991) and Rossello-Mora et al. (1995) as further described below.

Probe specificity was optimized by determining the temperature or formamide concentration necessary to achieve single base mismatch discrimination in slot blot or whole cell hybridization experiments, respectively. Strains with 0, 1, 2, and 3 mismatches with the target sequence were identified using the program Probe Check. Control strains were obtained from the American Type Culture Collection (ATCC; Rockville, Md.). *Zoogloea ramigera* ATCC 19544, *Z. ramigera* ATCC 25935, and strain mz1t were cultured on Stokes' medium (Wagner, 1995). *Pseudomonas fluorescense* ATCC 13525, *Comamonas testosteroni* ATCC 11996, and *Alcaligenes eutrophus* ATCC 17697 were cultured according to the recommendations of ATCC. Positive and negative control strains were used in all hybridization experiments with activated sludge samples.

Probing for known zoogloeal strains

Probing of RNA extracts from activated sludge samples in slot blot hybridization experiments with $^{32}$P-labeled ZRA, or whole cell hybridization with fluorescein labeled ZBE and ZRA (Rossello-Mora et al., 1995)did not result in detectable hybridization. Positive responses with 32P-labeled EUB 338 (control probe specific for all eubacteria, Wagner et al, 1993, *Appl. Environ. Microbiol.* 59:1520–1525) indicated that the RNA extraction procedure was effective, and microscopic examination of zoogloeal clusters probed with fluorescein labeled EUB 338 indicated successful penetration of the probe and hybridization with the organisms forming the clusters.

Isolation and cultivation of zoogloeal clusters

The zoogloeal cultures derived from micromanipulation of activated sludge yielded two major colony types distinguishable by size. The mzt strains formed small colonies on R2A/S agar plates, and grew in EASM and R2A/S liquid medium as flocs, whereas mzL strains formed large colonies on R2A/S agar plates, grew poorly in EASM medium, and grew as dispersed cells in R2A/S. The 16S rDNA genes from three representatives of the large colony type (mz1L, mz2L, and mz3L) and two of the smaller type (mz1t and mz2t) were amplified, cloned and sequenced in the base pair region 1100 to 1492. Additional sequencing of mz1t 16S rDNA in the base pair region 500–900 was performed for direct comparison with the targeted region of previously developed Zoogloea spp. probes.

Phylogenetic analysis and probe design

Comparison of both sequenced 16S rRNA regions of mz1t with sequences in the University of Illinois 16S Ribosomal Data Base Project (RDP) using the program Similarity Rank (Jun. 9, 1997; 20:05:02) yielded a closest match (0.82) with *Pseudomonas* sp. str. K172, clone K1(*Thauera aromatica*; Anders et al., 1995). Comparison with GenBank yielded a 97% similarity to a Proteobacteria 16S rDNA gene from strain mXyN1(unclassified, Rabus and Widdel, 1995) and *Thauera aromatica*. Similarity rank analysis for mz2L in the 16S rRNA region 1100–1492 yielded a closest match (0.84) with *Brachymonas denitrificans* str. AS-P1 (Hiraishi et al., 1995). Distance matrix tree analysis indicates that the mzt strains (mz1t and mz2t) are more closely related to *Z. ramigera* ATCC 19544 than are the mzL strains (mz1L, mz2L, and mz3L), and are probably members of the genus Thauera. Comparison of mz1t and *Z. ramigera* ATCC 19544 16S rRNA sequences indicates a 3 base pair mismatch in the ZRA probe target region.

Using the region 1100–1492 a probe was designed (Rhodo: 5'-ATCCGGACTACGATCGGC-3') to encompass *Z. ramigera* ATCC 19544 and the mzt strains. Probing of RDP using the program Probe Check indicated that the Rhodo probe is complementary to the 16S rRNA regions of 28 listed sequences, including primarily members of the genera Thauera, Azoarcus, Zoogloea, and Rhodocyclus. A probe was also designed for the mzt strains in the region targeted by the *Z. ramigera* probe ZRA (base pairs 647–664). This probe (MZ1; 5'-TCTGCCGTACTCTAGCCTT-3') has 3 base pair mismatches with *Z. ramigera* ATCC 19544 in the target region (see Table 2). Comparison of this probe with known sequences in RDP using Probe Check indicated that four complementary 16S rRNA sequences are present. These include one member of the genus Azoarcus (A. sp. BH72; Hurek et al., 1993), the two known representatives of the genus Thauera (*T. selenatis* and *T. aromatica*), and an unclassified strain (env. AX39). Many of the previously sequenced Azoarcus spp. have 1 mismatch with this probe.

TABLE 2

16S rRNA oligonucleotide probes.

| Probe | Target Strains | Sequence (5'-3') | Sequence Positions[a] |
|---|---|---|---|
| ZRA | *Z. ramigera* ATCC 19544 | CTGCCGTACTCTAGTTAT | 647–664 |
| ZBE | *Z. ramigera* ATCC 25935 | TGCCAAACTCTAGCCTTG | 646–663 |
| EUB | Eubacteria | GCTGCCTCCCGTAGGAGT | 338–355 |
| MZ1 | mzt, Thauera spp. | TCTGCCGTACTCTAGCCTT | 646–664 |
| Rhodo | mzt, Thauera spp., *Z. ramigera* ATCC 19544, Azoarcus spp., Rhodocyclus spp. | ATCCGGACTACGATCGGC | 1290–1309 |

[a]*E. coli* 16S rRNA numbering.

Using the program Probe Check, strains having 16S rRNA sequences with 0,1,2 and 3 mismatches with the probes ZRA, Rhodo and MZ1 were identified (see Table 3). The individual target strains and the number of mismatches which each probe are indicated in Table 2. Whole cell hybridization with fluorescently labeled probes indicated that a formamide concentration of 10% yielded two mismatch discrimination, whereas a concentration of 40% was required to achieve one mismatch discrimination.

TABLE 3

Number of mismatches between probe sequences and 16S rRNA sequences in target strains.

| | Probe Sequence | | |
|---|---|---|---|
| Target Strain[a] | ZRA | MZ1 | Rhodo |
| *Z. ramigera* ATCC 19544 (X74913) | 0 | 3 | 0 |
| mz1t | 3 | 0 | 0 |
| *Pseudomonas fluorescens* ATCC 13525 (L24790) | 4 | 5 | 1 |

TABLE 3-continued

Number of mismatches between probe sequences and 16S rRNA sequences in target strains.

| Target Strain[a] | Probe Sequence | | |
|---|---|---|---|
| | ZRA | MZ1 | Rhodo |
| Comamonas testosteroni ATCC 11996 (M11224) | 4 | 1 | 2 |
| Alcaligenes eutrophus ATCC 17697 (M32021) | 5 | 2 | 3 |
| Z. ramigera ATCC 25935 (X74914) | 5 | 2 | 3 |

[a]Designations in parenthesis refer to NCBI GenBank accession numbers

Whole cell hybridization with fluorescent probes

Whole cell (in situ) hybridizations of activated sludge were performed at formamide concentrations of 40% with the fluorescein labeled probes EUB, ZRA, MZ1 and Rhodo. Microscopic examination indicated that visible zoogloeal clusters probed strongly positive with the fluorescent probes EUB, MZ1 and Rhodo. These included zoogloeal clusters attached to or embedded in flocs and those found as separate clusters in the wastewater. Weak fluorescence was observed from some large filamentous forms with the MZ1 and Rhodo probes. No hybridization was observed with the ZRA probe. Probing with EUB yielded strong fluorescent hybridization signals from zoogloeal clusters, filaments and individual cells within the floc structure.

Novel zoogloea strains

Selective enrichment and separation techniques have been commonly utilized to isolate microorganisms believed to form zoogloeal clusters in activated sludge (Unz and Dondero, 1967; Unz and Farrah, 1972; Unz, 1984). The major limitation of these approaches is that it is difficult to verify that the organisms isolated are those forming clusters in the original samples. This is due to the lack of distinct biochemical traits used to distinguish members of the genus Zoogloea, the widespread ability of microorganisms to grow as flocs, the tendency for floc formation to be influenced by culture conditions, and the possibility that the causative organisms are not readily culturable. The 16S rRNA sequences of individual species are conserved irrespective of growth form (clusters, filaments, or dispersed cells) or culture conditions, and can be used to verify that the target strain was successfully isolated. This approach was used in this study for the isolation and identification of the organisms responsible for zoogloeal cluster formation, and was important in distinguishing between the two types of organisms observed (mzt and mzL strains).

Of the three Zoogloea spp. commonly utilized in activated sludge studies, only Z. ramigera ATCC 19544 has been proven to be of common occurrence, and tends to be associated with high organic loading (Rossello-Mora et al., 1995). However, the results presented here indicate that some strains that form zoogloeal clusters have not as yet been identified. Strain mz1t is significantly different from previously described Zoogloea spp. as determined by comparative 16S rRNA sequence analysis, and appears to be in the genus Thauera. There are only two previously described Thauera species, T. selenatis (Macy et al., 1993) and T. aromatica (Anders et al., 1995). T. aromatica can utilize a large variety of organic acids and aromatic compounds aerobically and with nitrate as an electron acceptor. The closely related strain mXyN1 grows on toluene, m-xylene, phenylacetate, and acetate under denitrifying conditions (Rabus and Widdel, 1995). These organisms have not been previously reported to form zoogloeal clusters in activated sludge.

Association of zoogloeal clusters with poor dewaterability

Correlation of the presence of zoogloeal clusters with poor sludge dewaterability, and verification of the mzt strains as the cluster forming organisms via whole cell hybridization with fluorescent probes, indicate that this is the responsible organism in the sludge dewatering problems observed at at least one wastewater treatment plant. Further confirmation is possible by RNA extraction of archived sludge samples and slot blot hybridization with the MZ1 and Rhodo probes to determine if dewatering potential can be correlated with the presence of strain mz1t throughout the entire study period. As mz1t has not been completely characterized, and appears to be a member of the relatively uncharacterized genus Thauera, it is not possible from identification alone to determine the environmental or operating conditions responsible for its growth and the dewatering problems related to its presence. It is not known whether zoogloeal cluster prevalence is exclusively determined by competitive growth on simple organic acids as determined by plant operating conditions, or if the more genus specific capability for aromatic degradation under anaerobic conditions is a contributing factor. However, the ability to obtain pure cultures of the causative organism allows further experiments to be performed to elucidate the ecological basis of the observed sludge quality problems.

Probing strategies

A nested approach was used in designing the Zoogloea spp. probes Rhodo and MZ1. In cases where the identity of the species comprising the zoogloeal clusters is not known it may be desirable to use the broadest probe possible. The Rhodo probe hybridizes with the Zoogloea type strain Z. ramigera ATCC 19544 and mz1t, both of which have now been demonstrated to be responsible for cluster formation in activated sludge. However, it is possible that due to its broad specificity it may hybridize to non-target species (i.e., species that do not form clusters) that possess the same or similar sequence. The MZ1 probe is much more specific, and results indicate that single mismatch discrimination can be achieved if necessary. However, this level of stringency can result in a diminished fluorescent signal from the target strain. The presence of single mismatch non-target strains may not be a problem in most wastewater treatment plants, and potential single mismatch targets include primarily members of the closely related genus Azoarcus (Zhou et al., 1995). The appropriate probe to use and the desired level of stringency ultimately is application dependent (Stahl and Amann, 1991). The use fluorescent labeled probes and epifluorescence microscopy when identifying causative organisms or during routine monitoring can insure against hybridization with non-target species.

Other novel sludge strains

The 16S rRNA sequences from the mzL strains are similar to other 16S rRNA sequences derived from PCR amplified 16S rDNA from total DNA extracts from this wastewater treatment plant (data not presented). The role of these strains is as yet uncertain. Fluorescent probes may be used to determine their location in the sludge flocs, and if they are associated with zoogloeal clusters.

EXAMPLE 2

Molecular Analysis of Hyphomicrobium spp. in Viscous Sludge

DNA Extraction and Purification

DNA from the sludge was extracted by a modified Ogram DNA extraction procedure (Ogram et. al., 1987). Sludge samples (150 ml) were spun at 6000×g in JA-14 fixed angle rotor in a J-21 series Beckman Centrifuge for 10 minutes.

The pellets obtained were treated with 50 ml of 0.12M sodium pyrophosphate buffer ($Na_4P_2O_7.0\ H_2O$) pH 8.0 and 2.5 ml of 5% (w/v) sodium dodecyl sulfate ($Cl_2H_{25}OSO_3Na$) then put in a 70° C. water bath for one hour with inversions by hand every ten minutes. The bacteria were then mechanically disrupted by using 5 g of 0.1 mm glass beads (approximately a 1:1 ratio of sample and glass beads) in a bead beater for 5 min with a pattern of 2 minutes ON, 1 minute OFF and 2 minutes ON. The sample was then cooled on ice, and the sample/glass bead mixture was centrifuged at 6000×g for 25 minutes at 10° C. and the supernatant recovered. Further recovery of DNA was done by successive extractions of the sediment with 0.12M sodium pyrophosphate, pH 8.0 by adding 50 ml of the buffer and centrifuging as above. Supernatants were pooled. Extracts were precipitated at −20° C. with 0.1 volume of 2M sodium acetate ($NaC_2H_3O_2.3H_2O$) and 0.8 volume isopropanol. The precipitates were centrifuged (10,000×g at 4° C. for 30 minutes) and dried using a Savant Speed Vac Concentrator to remove the residual alcohol. The dried sample was resuspended with TRIS ethylenediaminetetraacetate (TE) [10 mM Tris, 1 mM EDTA (pH 7.5–8.0)] buffer, dialyzed (to remove impurities such as salts) overnight in dialysis tubing (Mol wt cut off 6000–8000) against 1× (TE) buffer and extracted with phenol followed by chloroform/iso-amyl alcohol (24:1) to denature proteins. Sodium acetate (0.1 volume of 2M solution) was added, and the sample incubated at −20° C. to precipitate most of the humic materials (Ogram et. al., 1987). After centrifugation the supernatant was removed and two volumes of absolute ethanol were added to precipitate the purified DNA. The samples were centrifuged (10,000×g for 30 minutes at 4° C. and dried in a speed vac to remove the ethanol. The dried sample was resuspended in 1 ml sterile TE buffer. DNA was further purified using the Elu-Quick DNA purification kit from Schleicher and Schuell, New Hampshire. The purified DNA was treated with RNAse, and subsequently used for PCR amplification.

The optical density, at 260 nm, of a pure solution of double-stranded DNA at 50 µg/ml is 1.0 (Becker et al., 1990). Therefore, DNA concentration was estimated by measuring the absorption at 260 nm using a Beckman DU-70 spectrophotometer.

The samples which were originally brown, turned dark brown after bead beating, which could be due to the release of organic carbon from the combination of SDS and heat liberated during bead beating (Ogram et. al., 1987). DNA was further extracted by phenol-chloroform and concentrated by ethanol precipitation. Although the dark brown color was drastically reduced, the DNA sample still had a light brown color indicating the presence of contaminants, presumably humic materials. Therefore, DNA was further purified by using the Elu-Quick DNA purification kit to obtain an acceptable ratio of absorbance at 260 nm and 280 nm. RNAs in the sample were removed by RNAase treatment before the DNA was quantified using a Spectrophotometer (Becker et al., 1990). DNA yields were low and the $A_{260}/A_{280}$ ratio was below 1.5 for January and November sludge samples indicating either the presence of impurities in the samples or the degradation of DNA over a period of time after sampling.

Qiagen Protocol for the Purification of Total DNA

DNA extracted from sludge samples by the freeze-dried method was purified by the Qiagen protocol (Qiagen, Chatsworth, Calif.). 10 ml of equilibration buffer (QBT) containing NaCl, 750 mM; MOPS, 50 mM; ethanol, 15%; triton X-100, 0.15%, pH 7.0 was passed through the Qiagen column. DNA, resuspended in 10 ml TE buffer was then passed through the column. The column was then washed thrice with 15 ml of wash 1 buffer (NaCl, 50 mM; MOPS, 50 mM; ethanol, 15%; pH 7.0), once with 15 ml of wash 2 buffer (NaCl, 1000 mM; MOPS, 50 mM; ethanol, 15%; pH 7.0) and once with 15 ml of wash 3 buffer (NaCl, 1600 mM; MOPS, 50 mM; ethanol, 15%; pH 7.0). The eluate was saved after each wash step, and the DNA precipitated with 0.7 volumes of isopropanol, and centrifuged for 30 min. The pellets were washed with 70% ethanol, dried and resuspended in 1 ml TE buffer for further analysis. DNA concentration was measured in the absorbance range of 200–300 nm before and after purification.

PCR Amplification of 16S rDNA

The DNA coding for 16S rRNA was amplified from the purified genomic DNA of the activated sludge sample by PCR using primers complementary to the conserved regions in the 5' and 3' regions of the 16S rRNA genes of most organisms. The primers 27f: 5'-AGA GTT TGA TCM TGG CTC AG-3' (SEQ ID NO:21) and 1492r: 5'-TAC GGY TAC CTT GTT ACG ACT-3' (SEQ ID NO:22) were synthesized using an Oligo 1000 DNA synthesizer (Beckman, Fullerton, Calif.), and the synthesized primers were cleaved from the solid support in the reactor column. The protecting groups blocking the oligomers' reactive phosphoryl and amino groups were removed using the DNA Ultra Fasi cleavage and deprotection kit. Amplification was performed in a 100 µl reaction mixture (distilled water,75 µl; primers,2.5 µl each; dNTP's,2 µl each; buffer, 10 µl; template DNA,2 µl; Taq polymerase, 0.5 µl) in an automated thermal cycler (Perkin Elmer-Cetus) by denaturing samples at 99° C. for 5 min. and subsequent amplification by 38 cycles of denaturing (94° C./1 minute), annealing (45° C./1Y minute) and elongation (72° C./1 minute) plus an additional cycle with a final 10 minutes elongation at 72° C. to increase the yield of PCR products and to reduce the faint smear observed on the gel directly below the PCR product (Promega, Madison Wis.). The amplified samples were stored at 4° C. A negative control with no addition of template DNA was also included.

TABLE 4

16S rRNA sequencing primers and their specificity. Sequence for m13f (−40) and m13r were reproduced from the Invitrogen Manual. All other sequences were reproduced from Nucleic Acid Techniques in Bacterial Systematics Stackebrandt et al., 1991. Primers 27f, 1492r and 1525r were used for the amplification of 16S rDNA from the total DNA. Primers 530f, 907r, 926f, 1492r, m13f (−40), and m13r were used for 16S rDNA sequencing.

| Name | Sequence (5' - 3') | | Comments |
|---|---|---|---|
| 27f | AGAGTTTGATC(C/A)TGGCTCAG | (SEQ ID NO:23) | PCR and sequencing, most eubacteria |
| 109r1 | ACGVGTTAC(G/T)CACCCGT | (SEQ ID NO:24) | Broad specificity |
| 109r2 | A(G/T)(A/G)CATTACTCACCCGT | (SEQ ID NO:25) | Most gamma and some beta proteobacteria |

TABLE 4-continued 16S rRNA sequencing primers and their specificity. Sequence for m13f (−40) and m13r were reproduced from the Invitrogen Manual. All other sequences were reproduced from Nucleic Acid Techniques in Bacterial Systematics Stackebrandt et al., 1991. Primers 27f, 1492r and 1525r were used for the amplification of 16S rDNA from the total DNA. Primers 530f, 907r, 926f, 1492r, m13f (−40), and m13r were used for 16S rDNA sequencing.

| Name | Sequence (5' - 3') | | Comments |
|---|---|---|---|
| 342r | CTGCTGCS(C/T)CCCGTAG | (SEQ ID NO:26) | Most eubacteria |
| 357r | CTCCTACGGGAGGCAGCAG | (SEQ ID NO:27) | Most eubacteria |
| 519r | G(A/T)ATTACCGCGGC(G/T)GCTG | (SEQ ID NO:28) | Most eubacteria, eukaryotes, archaebacteria |
| 530f | GTGCCAGC(C/A)GCCGCGG | (SEQ ID NO:29) | Most eubacteria, eukaryotes, archaebacteria |
| 685r1 | TCTACG(A/G)ATTTCACC(C/T)CTAC | (SEQ ID NO:30) | Alpha and delta proteobacteria, fusobacteria |
| 685r2 | TCTACGCATTTCAC(C/T)GCTAC | (SEQ ID NO:31) | All beta and gamma proteobacteria |
| 685r3 | TCT(A/G)CGCTT(C/T)CACCGCTAC | (SEQ ID NO:32) | Most Gam-positive, cyanobacteria, some miscellaneous bacteria |
| 907r | CCGTCAATTC(C/A)TTT(A/G)AGTTT | (SEQ ID NO:33) | Most eubacteria, eukaryotes, archaebacteria |
| 926f | AAACT(C/T)AAA(G/T)GAATTGACGG | (SEQ ID NO:34) | Most eubacteria, eukaryotes, archaebacteria |
| 1100r | GGGTTGCGCTCGTTG | (SEQ ID NO:35) | Most eubacteria |
| 1114f | GCAACGAGCGCAACCC | (SEQ ID NO:36) | Most eubacteria |
| 1392r | ACGGGCGGTGTGT(A/G)C | (SEQ ID NO:37) | Most eubacteria eukaryotes, archaebacteria |
| 1406f | TG(C/T)ACACACCTCCCGT | (SEQ ID NO:38) | Most eubacteria, eukaryotes, archaebacteria |
| 1492r | TACGG(C/T)TACCTTGTTACGACTT | (SEQ ID NO:39) | PCR and sequencing, most eubacteria, archaebacteria |
| 1525r | AAGGAGGTG(A/T)TCCA(A/G) | (SEQ ID NO:40) | PCR and sequencing, most eubacteria, archaebacteria |
| m13f (−40) | GTTTTCCCAGTCACGAC | (SEQ ID NO:41) | |
| M13R | CAGGAAACAGCTATGAC | (SEQ ID NO:42) | |

Agarose Gel Electrophoresis of PCR Products

PCR amplified products (20 µl) and 2.5 µl of loading dye [50% glycerol, 1 mM EDTA(pH 8.0), 0.25% bromophenol blue and 0.25% xylene cyanol] were loaded into the wells and run on 1% (w/v) agarose gels in 1× TBE [prepared from 10× TBE stock solution (Tris base 108 g; Boric acid, 55 g; EDTA, disodium salt($C_{10}H_{14}O8N_2Na_2,2H_2O$), (0.5M; and distilled water, 1 liter; pH 8.0)] for approximately 2 hours at 80V (Sambrook et al, 1989) to check for the presence of an approximately 1500 bp 16S rDNA fragment by comparing it with DNA molecular weight markers run on the same gel. The gels were then stained with ethidium bromide (0.5 µg/ml) for 20 minutes and destained with de-ionized water for 20 to 30 minutes. The destained gels were then visualized on a Foto UV 300 DNA transilluminator (Fotodyne, New Berlin, Wis.), and the ethidium bromide-DNA complex was photographed with a Polaroid camera. Several approaches were compared for the further purification of the amplified 16S rDNA sequences as described below.

AgarACE Protocol for the Purification of PCR Amplified 16S rDNA

The PCR amplified 16S rDNA was further purified by AgarACE protocol (Promega, Madison, Wis.). PCR amplified products were run on 1% (w/v) agarose gels in 1× TBE solution for approximately 2 hrs at 80V. A slot was cut in front of the 1500 bp 16S rDNA fragment and the slot was filled with 1.8% LMP agarose. The gel was run again at 80V until the required band ran into IMP agarose which was cut and melted in an eppendorf tube at 65° C. 1 unit of AgarACE (5 µl) was added to the melted agarose and was incubated overnight. The AgarACE treated PCR products were purified by phenol/chloroform extraction and precipitated for 2 hours in 0.1 volume sodium acetate and 2 volume ethanol. The precipitated products were centrifuged (4° C.) at 14,000 rpm for 20 min, and dried in a speed vac for 20 min. The dried sample was resuspended in 200 µl TE buffer and used for further analysis.

Spin Column Protocol for the Purification of PCR Amplified 16S rDNA

PCR amplified products were run on 1% (w/v) agarose gels in 1× TBE solution for approximately 2 hours at 80V. The 1500 bp 16S rDNA fragment was cut and stored overnight in the refrigerator in a vial provided with a filter at the top. The PCR product was then centrifuged at 14,000×g for 15 minutes at 4° C. The top filter was removed after collecting the liquid in the bottom of the tube. Potassium acetate (0.1 volume) and ethanol (3 volumes) were added to the estimated volume in the bottom tube and stored in a freezer for at least 30 minutes. The precipitated sample was then centrifuged (4° C.) at 14,000×g for 15 minutes, washed with 70% ethanol and dried in speed vac. The dried sample was resuspended in 10 µl sterile TE buffer and used for further analysis.

Electroelution Protocol for the Purification of PCR Amplified 16S rDNA

PCR amplified products (35 µl each) were run on 0.8% agarose gel at 80V in two wells side by side. The gel around the 1500 bp band was cut and transferred into a dialysis bag containing 1 ml TE buffer. The gel was run again until the desired band in the excised gel moved into the TE buffer. TE buffer containing the PCR products was used for further analysis.

Cloning of 16S rRNA Genes 16S rDNA fragments amplified by PCR were ligated into a plasmid vector by using the Original TA Cloning kit (Invitrogen, San Diego, Calif.). The reaction mixture (10 µl) consisting of distilled water,5 µl; ligation buffer, 1 µl; vector, 2 µl; template DNA, 1 µl; and DNA ligase, 0.5 µl, was incubated overnight at 12° C., the INVαF' competent cells were transformed with the plasmids using the one-step TA cloning strategy. Frozen one shot competent cells (50µ) were mixed with 2 µl of 0.5M β-mercaptoethanol and 2 µl of ligation reaction. The reaction mixtures were incubated on ice for 30 minutes, and heat shock treatment was given to the cells for exactly 45 seconds (subsequently changed to 30 seconds by the manufacturer) in a 42° C. water bath, and the cell suspension was then placed on ice for 2 minutes. Aliquots of cell suspension in 250 µl SOC medium (room temperature) were plated onto Luria Bertani (LB) Agar medium (tryptone, 10 g/l; yeast extract, 5 g/l; NaCl, 10 g/l; agar 17% distilled water 1 liter pH 7.5) containing ampicillin (50 µg/ml and 25 µl of 40 mg/ml X-Gal, equilibrated at 37° C. for 30 minutes, and incubated overnight at 37° C. Colonies were selected for analysis after the agar plates were transferred to 4° C. for 2–3 hrs for proper color development (Invitrogen manual).

PCR Amplification of 16S rDNA from Clones

The white colonies picked using sterile toothpicks were streaked on LB agar containing ampicillin. The streaked colonies were then screened for plasmids containing full length (1500 bp) 16S rDNA inserts by PCR amplification of 16S rDNA using SP6 and T7 primers to distinguish between TA Cloning inserts and 16S rDNA from *Escherichia coli*. Primers were synthesized and purified as described above. The amplified products were run on 1% (w/v) agarose gel as described earlier to verify that the positive clones had 16S rDNA plasmid inserts.

Midiprep Plasmid Preparation from Strains with Inserts

Large amounts of plasmid DNA required for subsequent sequence analysis of 16S rDNA were prepared. The bacteria containing plasmids were grown on large scale (125 ml) harvested, and lysed by a modified Promega midiprep plasmid preparation method. (Promega, Madison, Wis.).

Bacteria were grown overnight in 125 ml LB broth in the presence of kanamycin (25 μg/ml) at 37° C. in a shaking incubator (Labline Instruments Inc., Melrose Park, Ill.). Cells (0.5 ml) were preserved in cryotubes with 0.5 ml of 30% sterile glycerol at −80° C., and the rest of the sample was centrifuged at 8,000×g for 10 minutes at 10° C. The pellets obtained were resuspended in 3 ml of cold lysis buffer. Six ml of freshly prepared 0.2 N sodium hydroxide (NaOH), 1% sodium dodecyl sulfate ($C_{12}H25OSO_3Na$) and 3.75 ml of 5M potassium acetate ($KC_2H_3O_2$) were added and the mixture was centrifuged for 30 minutes at 10,000×g. Equal volumes of isopropanol was added to the supernatant, and the samples were centrifuged at 10,000×g for 30 minutes. The pellet was washed with 70% ethanol and dried in a speed vac. The dried pellet was RNAse treated and purified by phenol chloroform extraction. The purified plasmids were dried, resuspended in 200 μl of TE buffer and stored at −80° C.

16S rDNA Sequencing

30 μl of plasmid containing the insert was sequenced for approximately 400 bp of the 1.5 kb 16S rDNA molecule by the single primer extension method using the 1492r primer (Table 4). Full length (1500 bp) 16S rRNA sequences amplified from an activated sludge isolate was determined using the primers m13f (SEQ ID NO:41), 530f (SEQ ID NO:30), 907r (SEQ ID NO:33) and m13r (SEQ ID NO:42) (Table 4). All primers were synthesized using an Oligo 1000 DNA synthesizer.

16S rDNA Sequence Analysis 16S rDNA sequences were analyzed using different software packages. The sequences were ranked against all organisms in the small subunit prokaryotes (SSU-Prok) rRNA database using SIMILARITY_RANK software available in the Ribosomal Database Project (Maidak et al., 1997, Van de Peer et al., 1997). The Genetics Computer Group's (GCG) sequence analysis software package (version 8.1 on UNIX) was used to cluster sequences by similarity to produce a dendrogram. Multiple sequence alignments from a group of related sequences using progressive, pairwise alignment were created by using the pileup function. Multiple sequence format (msf) files were then analyzed to create oligonucleotide probes specific for the desired target strain.

Phylogenetic trees based on the distance matrix method were constructed from the aligned sequences. Organisms belonging to the lineage of the Bacteria domains consisting of the α, β, γ and δ subclasses of the Proteobacteria, Cytophagales/Flavobacter/Flexibacter group, and Gram Positive organisms with Low (G+C) content were found in all three samples analyzed (January, April, November) of the activated sludge. Differences in the bacterial populations in each monthly sample analyzed were found. In April, organisms belonging to a subclass of Proteobacteria (50%) were dominant over the β subclass (23%), γ subclass (3.85%), cytophagales (11.54%), low G+C (3.85%) and unknown organisms (7.7%). However, in January, clones representing the β subclass of the Proteobacteria (44%) were dominant over the α (20%) and γ (20%) subclasses, the cytophagales group (4%), the δ subclass (4%), and the unknown group (8%). In November, members of the α subclass of the Proteobacteria (31.25%) were dominant over the β (18.75%) and γ (3.85%) subclasses, the cytophagales group (25%), the low G+C group (12.5%) and the unknown group (12.5%).

None of the clones were identical to any of the known 16S rRNA sequences in the database.

Hyphomicrobium spp. Probe Design

Multiple sequence alignments from a group of related sequences using progressive, pairwise alignment were created by using the pileup function. The pairwise evolutionary distances between the aligned sequences, expressed as substitutions per 100 bases, were obtained from the distance function of the GCG package. A multiple sequence format (msf) file containing the multiple sequence alignments of all the cloned sequences in the 16S rDNA sludge library was then analyzed to create oligonucleotide probes. The signature nucleotides [5' GCT GC(C/G) CAT TGT CAC CGC C 3'] for *Hyphomicrobium vulgare* and Hyphomicrobium-like organism 16S rDNA sequences retrieved from RDP were identified. The degeneracy of the probe was designed to encompass the degeneracy of Hyphomicrobium strains as observed in the 16S rDNA library created from samples of an activated sludge and RDP sequences as determined by multiple sequence alignment.

Sequence Analysis of 16S rDNA from Hyphomicrobium Species

To further validate the sequencing results, 16S rDNA was amplified from three identical samples of Hyphomicrobium M3 isolated from an activated sludge. Initially, the 16S rDNA from the positive clones were partially sequenced using m13f (SEQ ID NO:41), 926f (SEQ ID NO:34) and n13r (SEQ ID NO: 42) primers. The sequence aligned *Hyphomicrobium vulgare* with a mere 45% similarity.

The sequences were edited by deleting the sequence obtained using the 926f primer after the potential target site of the Hyphomicrobium probe, and this sequence was substituted with the complementary strand of the sequences obtained using the m13r primer up to the 1492 consensus region. This resulted in drastic increase in the percentage similarity between the replicate sequences from the same isolate (from 75% to 99%) and also with the published sequences in the RDP database [over 70% to both Hyphomicrobium-like organism (strain US 353) and *Hyphomicrobium vulgare*].

Two of the positive clones (3M3 and 6M3) were then sequenced using 530f and 907r sequencing primers to obtain the complete (~1500 bp) sequence of 16S rDNA. Comparison of these clones with reference bacteria in the RDP database indicated their relatedness to Hyphomicrobium-like organism strain US 353 and *Hyphomicrobium vulgare*).

Fluorescent in-situ Hybridization

Organisms

Hyphomicrobium strain M3, was isolated from an activated sludge. Hyphomicrobium MC-750 (ATCC 27500) and *Zoogloea ramigera* (ATCC 25935) were obtained from the American Type Culture Collection (ATCC), *Sphingomonas*

*capsulatea* (ATCC 14666) was obtained from the Center for Environmental Biotechnology, University of Tennessee, Knoxville. *Bradyrhizobium japonicum* (USDA 110) was obtained from the Dept. of Microbiology, University of Tennessee, Knoxville. Sphingmonas sp. strain A8AN3, and *Escherichia coli* were obtained from the culture collection at the Center for Environmental Biotechnology, University of Tennessee, Knoxville. The present hybridization methods can be applied to other bacteria.

Cultivation of Cells

Hyphomicrobium strains were grown on ATCC culture medium 656 [$KH_2PO_4$, 1.36 g/l; $Na_2HPO_4$, 2.15 g/l; $(NH_4)_2SO_4$, 0.5 g/l; $MgSO_4.7H_2O$, 0.2 g/l; trace solution ($CuCl_2$, 0.15 g;. $FeSO_4.7H_2O$, 0.1 g; $MnSO_4.H_2O$, 0.035 g; $Na_2MoO_4.2H_2O$, 0.05 g; distilled water, 100 ml) 5.0 ml/l; filter sterilized methylamine hydrochloride, 3.38 g/l; Agar Noble (Difco 0142), 18.0 g/l; distilled water, 1 liter; pH 7.1] at 30° C. *Bradyrhizobium japonicum* was grown on RDY medium [yeast extract, 1 g/l; $K_2HPO_4$, 0.12 g/l; $MgSO_4$, 0.1 g/l; trace element ($H_3BO_3$, 3 g/l $MnSO_4.4H_2O$, 2.23 g/l; $ZnSO4.7H_2O$, 0.29 g/l; $CuSO_4.5H_2O$, 0.125 g/l; $COCl_2$, 0.065 g/l; $Na_2MoO4.2H_2O$, 0.12 g/l; 1 mM $FeCl_3$), 1 ml/l; L-glutamate, 1.0 g/l; Na-gluconoate, 5.0 g/l, distilled water, 1 liter; pH 7.0] at 30° C. Sphingomonas capsulate and Sphingomonas strain A8AN3 were grown on Nutrient broth (8.0 g/l peptone) pH 7.0 at room temperature. *Zoogloea ramigera* strain 25935 was grown on Stokes medium [Peptone, 5 g; 100× stock ($MgSO_4.7H_2O$, 20 g; $NH_4SO_4$, 7.5 g; Sodium citrate, 10 g; $CaCl_2$, 5 g; $MnSO_4$, 5 g; $FeCl_3.6H_2O$, 1 g, $FeSO_4$, 7.5 g; distilled water, 1 liter), 2 rnl; pH 7.2 at 30° C. *Escherichia coli* was grown on LB agar at 37° C.

Fixation of Culture Cells

Cells were harvested during the exponential growth phase to optimize the rRNA content. Cultured cells (1.7 ml) were spun at 14,000×g for 5 minutes. 750 µl of the supernatant was removed and the bacterial cells were fixed with equal volumes of 4% paraformaldehyde (Sigma, Mo.) in 0.2M sodium phosphate buffer (pH 7.2) for 3–24 hrs at 4° C. (Amann et al., 1990).

The incubated cells were sonicated for 5 minutes in an ice water bath and spun at 6,000×g for 5 min. Pellets were resuspended in 900 µl 1× PBS (130 mM NaCl in 30 mM NaPO4 buffer, pH 7.2) buffer and 100 µl 0.1l% Igepal, and spun at 6,000×g for 5 minutes. Cells were resuspended again in 500 µl 0.1% Igepal, vortexed, and spun at 6,000×g for 5 minutes. Pellets were resuspended in 200 µl 2× storage buffer [40 mM Tris pH 7.5, 0.2% Igepal CA-630 (Sigma, Mo.)], vortexed for at least 1 minute, and mixed with equal volumes of 96% ethanol and stored at −20° C.

Fixation of Sludge Samples

Activated sludge samples (10 ml) were centrifuged at 2,000×g for 5 minutes in sterile corex tubes. One ml of the supernatant was pipetted to a 1.7 ml eppendorf tube, and centrifuged at 14,000×g fol 5 minutes. Supernatant (750 µl) was removed, and was replaced by an equal volume (750 µl) of 4% paraformaldehyde (Sigma, Mo.) in 0.2M sodium phosphate buffer (pH 7.2) to fix the cells. The formaldehyde treated cells were vortexed for 1 minute, and incubated for 3–24 hrs at 4° C.

The incubated cells were centrifuged at 14,000×g for 5 minutes, and the supernatant was replaced with 10 mM EDTA. The cells were then sonicated for 10 minutes in an ice water bath and spun at 3,000×g for 5 min. Pellets were resuspended in 900 µl 1× PBS (130 mM NaCl in 30 mM NaPO4 buffer, pH 7.2) buffer and 100 µl 0.1% Igepal and spun at 3,000×g for 5 minutes. Cells were resuspended again in 500 µl 0.1% Igepal, votexed and spun at 3,000×g for 5 minutes. Pellets were resuspended in 200 µl 2× storage buffer, vortexed for at least a minute and mixed with equal volumes of 96% ethanol and stored at −20° C.

Hybridization

3 µl of each sample of fixed cells was placed on a poly-lysine coated slide, air dried, dehydrated in an ethanol series (50, 80 and 100%) for 3 minutes each, and air dried. Hybridization solution (9 µl) consisting of 5M NaCl, 1 M Tris pH 7.2, 10% SDS and distilled water, pH 7.2, with various concentrations (0, 10, 25, 30, 35, 45 and 75%) of formamide [stock solution of formamide was prepared by stirring formamide (40 ml) and 5 g mixed-bed ion-exchange resin (25–50 mesh, Bio-Rad AG 501-X8) at room temperature for 30 minutes. The resin treated formamide was filtered twice through Whatman No. 1 filter paper] were added. The slides were transferred to a hybridization chamber with 1M Whatman paper equilibrated earlier with equilibration buffer (30% formamide, 0.9M NaCl, 0.1% SDS, 100 mM Tris pH 7.2]. The slides were incubated at 37° C. for 30 minutes (Poulsen et.al., 1993). The Whatman paper was used to prevent drying during the hybridization process. The pre-hybridized cells were then exposed to 1 µl of 25–50 ng/µl degenerate Hyphomicrobium probe [5'GCT GC(C/G) CAT TGT CAC CGC C 3'] labeled with fluorescein (Genosys, The Woodlands, Tex.) and incubated overnight at 37° C. The appropriate formamide concentration needed to achieve the desired probe specificity was determined using formamide concentrations of 0, 10, 25, 30, 35, 45 and 75%.

Washing

The hybridized cells were rinsed with distilled water, incubated in a coplin jar with 100 ml of appropriate concentrations of hybridization solution (pre-warmed to 37° C.) for 20 minutes, rinsed with distilled water, and incubated in a coplin jar containing 100 ml of washing solution [4 ml 5M NaCl, 10 ml 0.5M sodium phosphate buffer (stock: 28 ml 0.5M $NaH_2PO_4$ and 72 ml 0.5M $Na_2HPO_4$), 1 ml 10% SDS, 1 ml 0.5M EDTA and 84 ml distilled water] at 37° C. for 15 minutes. The washed slides were dipped in 100 ml of distilled water and air dried.

A drop of anti fade solution (Vectashield mounting medium for fluorescence, H-1000, Vector Laboratories, Inc. Burlingame, Calif.) was added to the hybridized cells, and the cells were covered with a glass cover slip. The bacterial cells were visualized using an oil immersion objective (1000×). Fluorescence was detected with a microscope fitted for fluorescence microscopy, and photographs were taken. Exposure times were 0.01–0.05s for phase contrast and 20–40s for fluorescence micrographs.

Light Microscopy

A thick section (1 µm) was obtained from the embedded sample by cutting it with a glass knife using a Reichert Ultramicrotome. The section was then treated with a drop of 10% acetone on a gelatin coated glass slide. The slide was dried over a slide warmer and stained with 1% Toluidine Blue in 1% Borax and observed under a light microscope.

Negative staining

The sludge sample was settled on a glow discharged, carbon coated formvar grid for 1 minute, and was then treated with a drop of stain containing 0.25% phosphotungstic acid (pH 7.0 with KOH) and 2% uranyl acetate, pH 4.5, dried and observed with a Hitachi H-600 transmission electron microscope.

Fluorescent In Situ Hybridization Results

The ability of the degenerate fluorescent Hyphomicrobium probe to hybridize with the target sequence was examined using the cultured strains of the unreported Hyphomicrobium sp. M3 previously from sludge and *Hyphomicrobium vulgare* obtained from ATCC. The degenerate probe was also targeted for Hyphomicrobium species in the sludge. Binding of the probe was seen at all formamide concentrations. The specificity and sensitivity of the probe was further evaluated by hybridization to mixtures of morphologically distinct strains with known mismatches within the target sequence. Organisms with zero, one, two, four and eight mismatches in the probe target region as determined from the Check Probe tool of the RDD database were selected to check for probe specificity. The stringency of hybridization, to differentiate between organisms with mismatches in the probe target region, was determined by increasing the formamide concentration in the hybridization buffer while keeping the temperature constant at 37° C. Effective binding of the probe to Hyphomicrobium M3 and *Hyphomicrobium vulgare* was observed at all formamide concentrations. The results of mismatch discrimination experiments are summarized in Table 5.

TABLE 5

Hybridization of genomic DNA of control strains with the Hyphomicrobium probe targeting the 5'GCT GC(C/G) CAT TGT CAC CGC C 3' region of the 16S rRNA at various stringency levels.

| Strain | % Formamide concentration | | | |
|---|---|---|---|---|
| | 10 | 30 | 45 | 70 |
| M3 | + | + | + | + |
| Hyphomicrobium vulgare (ATCC 27500) | + | + | + | + |
| Sphingomonas capsulata (ATCC 14666) | + | + | + | + |
| Bradyrhizobium japonicum (USDA 110) | + | + | +/− | − |
| Zoogloea ramigera (ATCC 25935) | +/− | − | − | − |
| Sphingomonas A8AN3 | − | − | − | − |
| Escherichia coli | − | − | − | − |

The probe distinguished Sphingomonas A8AN3 and *Escherichia coli* from Hyphomicrobium M3 at 10% formamide concentration. *Zoogleoea ramigera* and *Bradyrhizobium japonicum* were distinguished from Hyphomicrobium species at 30% and 70% formamide concentrations, respectively. Unexpectedly, at 10% formamide concentration, the probe bound to *Zoogleoea ramigera* with 8 mismatches but not to Sphingomonas A8AN3 that has four mismatches. Although the amount of bound probe gradually decreased, as expected, by increasing the formamide concentration, the probe still showed binding to *Hyphomicrobium vulgare* and *Sphingomonas capsulata* at 70% formamide concentration.

Microscopic Examination of Activated Sludge

Microscopic examinations for morphological characteristics were made using light microscopy, transmission electron microscopy (TEM) and scanning electron microscopy (SEM) to further confirm the legitimacy of phylogenetic trees (presence of Hyphomicrobium spp.) obtained by 16S rRNA analysis.

Organisms with various morphologies were observed. Cell septa which could hardly be seen under light microscopy were visible under transmission and scanning electron microscopy. Organisms resembling Hyphomicrobium [a group of gram-negative (Holm et al., 1996) organisms consisting of cells (0.5 to 1.0×1.3 μm) which are either rod-shaped with pointed ends, oval- or bean- shaped, and produce mono- or bipolar filamentous outgrowths (prosthecae or hyphae) of varying length and capable of utilizing one carbon compounds such as methane (Lee et al., 1996) or methylamine (Harder et al.) for growth], Zoogloea spp. and filamentous bacteria were observed. The identification of the isolates as budding and prosthecate bacteria (Hyphomicrobium, Hyphomonas, Pedomicrobium) was based on the budding morphology and their ability to produce prosthecae (Staley et al., 1988).

REFERENCES

Altshul, S. F., Gish, W., Miller, W., Myers, E. W., and Lipman, D. L. (1990) "Basic local alignment search tools." *J. Mol. Biol.,* Vol. 215, pp. #403–410.

Amann, R. I., Binder, B. J., Olsen, R. J., Chisholm, S. W., Devereux, R., and Stahl, D. A. (1990a) "Combination of 16S rRNA-targeted oligonucleotide probes with flow cytometry for analyzing mixed microbial populations." *Appl. Environ. Microbiol.,* Vol. 56, No. 6, pp. #1919–1925.

Amann, R. I., Krumholz, L., and Stahl, D. A. (1990b) "Fluorescent-oligonucleotide probing of whole cells for determinative, pylogenetic, and environmental studies in microbiology." *J. Bacteriol.,* Vol. 172, No. 2, pp. #762–770.

Amaral, J. A., Archambault, C., Richards, S. R., Knowles, R. (1995) "Denitrification associated with Groups I and II methanotrophs in a gradient enrichment system. *FEMS Microbiology Ecology* 18, 289–298.

Anders, H. J., Kaetzke, A., Kampfer, P., Ludwig, W., and Fuchs, G. (1995) "Taxonomic position of aromatic-degrading denitrifying pseudomonad strains K 172 and KB 740 and their description as new members of the genus Thauera, as *Thauera aromatica* sp. nov., and Azoarcus, as *Azoarcus evansii* sp. nov., respectively, members of the Beta Subclass of the Proteobacteria." *Int. J. Syst. Bacteriol.,* Vol. 45, No. 2, pp. #327–333.

Barber, J. B., Bullard, C. M., and Charles, A. M. (1995) "Activated sludge process control based on sludge dewatering potential." Paper presented at The 68th Annual Conference & Exposition, Water Environment Federation, Miami Beach, Fla.

Becker 1990

Bradford 1997

Bullard, C. M., and Barber, J. B. (1994) "Improved operational performance using an extended sludge reaeration process." Paper presented at The 67th Annual Conference & Exposition, Water Environment Federation, Chicago, Ill.

Crabtree, K., and McCoy, E. (1967) "*Zoogloea ramigera* Itzigsohn, identification and description." *Int. J. Syst. Bacteriol.,* Vol. 17, pp. #1–10.

Friedman, B. A., and Dugan, P. R. (1968) "Identification of Zoogloea species and the relationship to zoogloeal matrix and floc formation." *J. Bacteriol.,* Vol. 95, pp. #1903–1909.

Harder, W., Attwood, M. M. ( ) "Biology, physiology and biochemistry of Hyphomicrobia." ( ) 303–359.

Hertel, C., Ludwig, M., Obst, M., Vogel, R. F., Hammes, W. P., and Schleiffer, K. H. (1991) "23S rRNA-targeted oligonucleotide probes for the rapid identification of meat lactobacilli." *Syst. Appl. Microbiol.,* Vol. 14, pp. #173–177.

Hiraishi, A., Shin, Y., and Sugiyama (1995) "*Brachymonas denitrificans* gen. nov., an aerobic chemoorganotrophic bacterium which contains rhodoquinones, and evolutionary relationships of rhodoquinone producers to bacterial species with various quinone classes." *J. Gen. Appl. Microbiol.,* Vol. 41, pp. #99–117.

Holm, N. C., Gliesche, C. G., Hirsch, P. (1996) "Diversity and structure of Hyphomicrobium populations in a sewage treatment plant and its adjacent receiving lake." *Applied and Environmental Microbiology,* 62(2), 522–528.

Hurek, T., Burggraf, S., Woese, C. R., and Reinhold-Hureck, B. (1993) "16S rRNA-targeted polymerase chain reaction and oligonucleotide hybridization to screen for Azoarcus spp., grass associated diazotrophs." *Appl. Environ. Microbiol.,* Vol. 59, No. 11, pp. #3816–3824.

Lane, D. J. (1991) "16S/23S rRNA sequencing." in: *Nucleic Acid Techniques in Bacterial Systematics* (E. Stackerbrandt and M. Goodfellow, eds.), John Wiley & Sons, Chichester, West Sussex, pp. #115–148.

Lee, S., Bollinger, J., Bezdicek, D., Ogram, A. (1996) "Estimation of the abundance of an uncultured soil bacterial strain by a competitive quantitative PCR method" *Applied and Environmental Microbiology* 62(10), 3787–3793. Macy, J. M., Rech, S., Auling, G., Dorsch, M., Stackebrandt, E., and Sly, L. I. (1993) "*Thauera selenatis* gen. nov., sp. nov., a member of the beta subclass of Proteobacteria with a novel type of anaerobic respiration." *Int. J. Syst. Bacteriol.,* Vol. 43, No. 1, pp. #135–142.

Maidak, B. L., Larsen, N., McCaughey, M. J., Overbeck, R., Olsen, G. J., Fogel, K., Blandy, J., and Woese, C. R. (1994) "The ribosomal database project." *Nucleic Acids Research,* Vol. 22, pp. #3485–3487.

Maidak, B. L., Olsen, G. J., Larsen, N., Overbeek, R., McCaughey, M. J., Woese, C. R. (1997) "The RDP (Ribosomal Database project)." *Nucleic Acid Research,* 25(1), 109–110

Ogram, A., Sayler, G. S., Barkay, T. (1987) "The extraction and purification of microbial DNA from sediments." *Journal of Microbiological Methods* 7, 57–66 (1987).

Poulsen, L. K., Ballard, G., Stahl, D. A. (1993) "Use of rRNA fluorescence in situ hybridization for measuring the activity of single cells in young and established biofilms." *Applied and Environmental Microbiology,* 59(5), 1354–1360.

Rabus, R., and Widdel,F. (1995) "Anaerobic degradation of ethylbenzene and other aromatic hydrocarbons by new denitrifying bacteria." *Arch. Microbiol.,* Vol. 163, pp. #90–103.

Reyes, F. L., Ritter, W., Raskin, L. (1997) "Group-specific small-subunit rRNA hybridization probes to characterize filamentous foaming in activated sludge systems. *Applies and Environmental Microbiology* 63(3), 1107–1117.

Rossello-Mora, R., Wagner, M., Amann, R., and Schleiffer, K. -H. (1995) "The abundance of *Zoogloea ramigera* in sewage treatment plants." *Appl. Environ. Micro.,* Vol. 61, No. 2, pp. #702–707.

Sambrook et al., (1989) *Molecular Cloning: A Laboratory Manual,* 2nd Ed., Cold Spring Harbor Laboratory, Cold Spring Harbor, N.Y.

Shin, Y. K., Hiraishi, A., and Sugiyama, J. (1993) "Molecular systematics of the genus Zoogloea and emendation of the genus." *Int. J. Syst. Bacteriol.,* Vol. 43, No. 4, pp. #826–831.

Stahl, D. A., and Amann, R., (1991). "Development and application of nucleic acid probes." in: *Nucleic Acid Techniques in Bacterial Systematics* (E. Stackerbrandt and M. Goodfellow, eds.), John Wiley & Sons, Chichester, West Sussex, pp. #205–242.

Staley, J. T., Fuerst, J. A. (1988) "Budding and/or appendaged bacteria." *Bergey's Manual of Bacteriology,* (Section 21), 1890–1904.

Unz, R. F. (1971). "Neotype strain of *Zoogloea ramigera* Itzigsohn." *Int. J. Syst. Bacteriol.,* Vol. 21, pp. #91–99.

Unz, R .F. (1984). "Genus IV. Zoogloea Itzigsohn." in: *Bergey's Manual of Systematic Bacteriology* (N. R. Krieg and J. G. Holt, eds.), Williams and Wilkins, Baltimore, Md. Vol. 1. pp. #214–219.

Unz, R. F., and N. C. Dondero. (1967) "The predominant bacteria in natural zoogloeal colonies. I. Isolation and identification." *Can. J. Microbiol.,* Vol. 13, pp. #1671–1682.

Unz, R. F., and S. R. Farrah (1972) "Use of aromatic compounds for growth and isolation of Zoogloea." *Appl. Microbiol.,* Vol. 23, pp. #524–530.

Van de Peer, Y., Jansen, J., Peter de Rijk and Rupert De Wachter, R. (1997) "Database on the structure of small ribosomal subunit RNA." *Nucleic Acids Res.,* 25(1), 111–116.

Wagner, M., Amann, R., Lemmer,H., Schleifer, K. (1993) "Probing activated sludge with oligonucleotides specific for Proteobacteria: Inadequacy of culture dependent methods for describing microbial community structure." *Applied and Environmental Microbiology* 59(5), 1520–1525.

Wagner, M., Amann, R., Kampfer, P., Assmus, B., Hartman, . . . , Hutzler, P., Springer, N., Schleifer, K. (1994) "Identification and in situ detection of gram-negative filamentous bacteria in activated sludge." *Syst. Appl. Microbiol.* 17, 405–417.

Wagner M., Erhart, R., Manz, W., Amann, R., Lemmer, H., Wedi, D., Schleifer, K. (1994), "Development of an rRNA-targeted oligonucleotide probe specific for the genus Acinetobacter and its application for in situ monitoring in activated sludge. *Applied and Environmental Microbiology* 60(3), 792–800.

Wagner, M. (1995) "Die Anwendung von in situ Hybridisierungssonden zur Aufklarung mikrobieller Populationsstrukturen in der Abwasserreinigung." Ph.D. Thesis, Technische Universitat Munchen.

Wagner, M., Rath, G., Amann, R., Koops, H. P., and Schleiffer, K. -H. (1995). "In situ identification of ammonia-oxidizing bacteria." *System. Appl. Microbiol.,* Vol. 18, pp. #251–264.

Zhou, J., Fries, M. R., Chee-Sanford, J. C., and Tiedje, J. M. (1995) "Phylogenetic analyses of a new group of denitrifiers capable of anaerobic growth on toluene and description of *Azoarcus tolulyticus* sp. nov." *Int. J. Syst. Bacteriol.,* Vol. 45, No. 3, pp. #500–506.

What is claimed is:

1. An isolated nucleic acid comprising the nucleic acid of SEQ ID NO:1.

2. An isolated nucleic acid comprising the nucleic acid of SEQ ID NO:2.

3. An isolated nucleic acid consisting of the nucleic acid of SEQ ID NO:1.

4. An isolated nucleic acid consisting of the nucleic acid of SEQ ID NO:2.

5. A method of detecting the presence of zoogloeal clusters in a wastewater sample, comprising:
    a) contacting DNA from a sample of the wastewater with the nucleic acid of claim 1 under conditions that permit specific hybridization; and
    b) detecting the presence of hybridization, the presence of hybridization indicating the presence of zoogloeal clusters.

6. A method of detecting the presence of zoogloeal clusters in a wastewater sample, comprising:
    a) contacting DNA from a sample of the wastewater with the nucleic acid of claim 2 under conditions that permit specific hybridization; and
    b) detecting the presence of hybridization, the presence of hybridization indicating the presence of zoogloeal clusters.

7. A method of detecting the presence of the Thauera sp. isolate mz1t in a wastewater sample, comprising:
    a) contacting DNA from a sample of the wastewater with the nucleic acid of claim 2; under conditions that permit specific hybridization; and
    b) detecting the presence of hybridization, the presence of hybridization indicating the presence of the Thauera sp. isolate mz1t.

8. A method of detecting the presence of the Thauera sp. isolate mz2t in a wastewater sample, comprising:
    a) contacting DNA from a sample of the wastewater with the nucleic acid of claim 2; under conditions that permit specific hybridization; and
    b) detecting the presence of hybridization, the presence of hybridization indicating the presence of the Thauera sp. isolate mz2t.

9. A method of detecting bacteria in sludge that are associated with sludge dewatering problems, comprising:
    a) contacting DNA from the bacteria with the nucleic acid of claim 1 under conditions that permit specific hybridization; and
    b) detecting the presence of hybridization, the presence of hybridization indicating the presence of a bacterium associated with sludge dewatering problems.

10. A method of detecting bacteria in sludge that are associated with sludge dewatering problems, comprising:
    a) contacting DNA from the bacteria with the nucleic acid of claim 2 under conditions that permit specific hybridization; and
    b) detecting the presence of hybridization, the presence of hybridization indicating the presence of a bacterium associated with sludge dewatering problems.

11. A method of detecting bacteria in sludge that are associated with sludge dewatering problems, comprising:
    a) contacting DNA from the bacteria with the nucleic acid of SEQ ID NO: 1 and the nucleic acid of SEQ ID NO: 2 under conditions that permit specific hybridization; and
    b) detecting the presence of hybridization, the presence of hybridization indicating the presence of a bacterium associated with sludge dewatering problems.

12. A method of detecting the presence of zoogloeal clusters in a wastewater sample, comprising:
    a) contacting DNA from a sample of the wastewater with the nucleic acid of claim 3 under conditions that permit specific hybridization; and
    b) detecting the presence of hybridization, the presence of hybridization indicating the presence of zoogloeal clusters.

13. A method of detecting the presence of zoogloeal clusters in a wastewater sample, comprising:
    a) contacting DNA from a sample of the wastewater with the nucleic acid of claim 4 under conditions that permit specific hybridization; and
    b) detecting the presence of hybridization, the presence of hybridization indicating the presence of zoogloeal clusters.

14. A method of detecting the presence of the Thauera sp. isolate mz1t in a wastewater sample, comprising:
   a) contacting DNA from a sample of the wastewater with the nucleic acid of claim 4; under conditions that permit specific hybridization; and
   b) detecting the presence of hybridization, the presence of hybridization indicating the presence of the Thauera sp. isolate mz1t.

15. A method of detecting the presence of the Thauera sp. isolate mz2t in a wastewater sample, comprising:
   a) contacting DNA from a sample of the wastewater with the nucleic acid of claim 4; under conditions that permit specific hybridization; and
   b) detecting the presence of hybridization, the presence of hybridization indicating the presence of the Thauera sp. isolate mz2t.

16. A method of detecting bacteria in sludge that are associated with sludge dewatering problems, comprising:
   a) contacting DNA from the bacteria with the nucleic acid of claim 3 under conditions that permit specific hybridization; and
   b) detecting the presence of hybridization, the presence of hybridization indicating the presence of a bacterium associated with sludge dewatering problems.

17. A method of detecting bacteria in sludge that are associated with sludge dewatering problems, comprising:
   a) contacting DNA from the bacteria with the nucleic acid of claim 4 under conditions that permit specific hybridization; and
   b) detecting the presence of hybridization, the presence of hybridization indicating the presence of a bacterium associated with sludge dewatering problems.

18. An isolated nucleic acid consisting of the nucleic acid of SEQ ID NO: 16.

19. An isolated nucleic acid consisting of the nucleic acid of SEQ ID NO: 17.

20. The nucleic acid of claim 18, wherein the nucleic acid specifically hybridizes to a nucleic acid of the genus Hyphomicrobium.

21. The nucleic acid of claim 19, wherein the nucleic acid specifically hybridizes to a nucleic acid of the genus Hyphomicrobium.

22. A method of detecting the presence of a Hyphomicrobium species in a wastewater sample, comprising:
   a) contacting DNA from a sample of the wastewater with the nucleic acid of claim 18 under conditions that permit specific hybridization; and
   b) detecting the presence of hybridization, the presence of hybridization indicating the presence of a Hyphomicrobium species.

23. A method of detecting the presence of a Hyphomicrobium species in a wastewater sample, comprising:
   a) contacting DNA from a sample of the wastewater with the nucleic acid of claim 19 under conditions that permit specific hybridization; and
   b) detecting the presence of hybridization, the presence of hybridization indicating the presence of a Hyphomicrobium species.

24. A method of detecting bacteria in sludge that are associated with sludge compaction problems, comprising:
   a) contacting DNA from the bacteria with the nucleic acid of claim 18 under conditions that permit specific hybridization; and
   b) detecting the presence of hybridization, the presence of hybridization indicating the presence of a bacterium associated with sludge compaction problems.

25. A method of detecting bacteria in sludge that are associated with sludge compaction problems, comprising:
   a) contacting DNA from the bacteria with the nucleic acid of claim 19 under conditions that permit specific hybridization; and
   b) detecting the presence of hybridization, the presence of hybridization indicating the presence of a bacterium associated with sludge compaction problems.

* * * * *

UNITED STATES PATENT AND TRADEMARK OFFICE
CERTIFICATE OF CORRECTION

PATENT NO. : 6,124,094
DATED : September 26, 2000
INVENTOR(S) : Lajoie, et al.

It is certified that error appears in the above-identified patent and that said Letters Patent is hereby corrected as shown below:

Table 1,
Delete "garget" and insert therefor -- target --.

Column 19,
Line 4, delete "(Cl$_2$H$_{25}$OSO$_3$Na) and insert therefor -- "C$_{12}$H$_{25}$OSO$_3$Na) --.

For any instance in which any of the following terms is not italicized, delete it and insert therefor the italicized term: *Hyphomicrobium, Zoogloea, ramigera, Thauera, Azoarcus, in situ, Rhodocyclus* and *Brachymonas*.

Claim 5,
Line 1, after "of" and before "clusters" delete "zooglocal"and insert therefor
-- zoogloeal --.

Claim 7,
Line 4, after "claim 2" please delete the semicolon.

Claim 8,
Line 4, after "claim 2" please delete the semicolon.

Claim 14,
Line 4, after "claim 4" please delete the semicolon.

Claim 15,
Line 4, after "claim 4" please delete the semicolon.

Claims 7, 8, 14 and 15,
For any instance in which the term "Thauera" is not italicized, please delete it and insert therefor -- *Thauera* --.

UNITED STATES PATENT AND TRADEMARK OFFICE
CERTIFICATE OF CORRECTION

PATENT NO. : 6,124,094
DATED : September 26, 2000
INVENTOR(S) : Lajoie, et al.

It is certified that error appears in the above-identified patent and that said Letters Patent is hereby corrected as shown below:

<u>Claims 20, 21, 22 and 23,</u>
For any instance in which the term "Hyphomicrobium" is not italicized, please delete it and insert therefor -- *Hyphomicrobium* --.

Signed and Sealed this

Thirteenth Day of November, 2001

*Attest:*

*Nicholas P. Godici*

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (xi) SEQUENCE DESCRIPTION: SEQ ID NO:1:

ATCCGGACTA CGATCGGC                                                    18

(2) INFORMATION FOR SEQ ID NO:2:

(i) SEQUENCE CHARACTERISTICS:
           (A) LENGTH: 619 base pairs
           (B) TYPE: nucleic acid
           (C) STRANDEDNESS: single
           (D) TOPOLOGY: linear (xi) SEQUENCE DESCRIPTION: SEQ ID NO:2:

TCCGGTGCGA GCGTTAATCG GAATTACTGG GCGTAAAGCG TGCGCAGGCG GTTTTGTAAG       60

ACAGATGTGA AATCCCCGGG CTTAACCTGG GAACTGCGTT TGTGACTGCA AGGCTAGAGT      120

ACGGCAGAGG GGGGTGGAAT TCCTGGTGTA GCAGTGAAAT GCGTAGAGAT CAGGAGGAAC      180

ACCGATGGCG AAGGCAGCCC CCTGGGCCTG TACTGACGCT CATGCACGAA AGCGTGGGGA      240

GCAAACAGGA TTAGATACCC TGGTAGTCCA CGCCCTAAAC GATGTCGACT AGTCGTTCGG      300

AGCAGCAATG CACTGAGTGA CGCAGCTAAC GCGTGAATTC GACCGCCTGG GGAGTTACGG      360

CCGCAAGGTT AAAACTCAAA GGAATTGACG GGACCCGCA CAAGCGGTGG ATGATTTGGA       420

TTAATTCGAT GCAACGCGAA AAACCTTACC TACCCTTGGC ATGTCTGGAA CCTTGCTGAN      480

AAGCNAGGTT GCCTTCCGGA NCCAGAACAC AGTTGCTGCA TGCTGTCGTC ACTCGTGTCC      540

TGANATGTTN GGTTNAATTC CCCCACAACG CACCCTGTCC CTAATTTGCC TCANTTGGTT      600

GGCCTCTATA AACCNACCN                                                  619

(2) INFORMATION FOR SEQ ID NO:3:

(i) SEQUENCE CHARACTERISTICS:
           (A) LENGTH: 579 base pairs
           (B) TYPE: nucleic acid
           (C) STRANDEDNESS: single
           (D) TOPOLOGY: linear (xi) SEQUENCE DESCRIPTION: SEQ ID NO:3:

ACTCAAAGGA TGGGCACGGG GACCCGCACA AGCGGTGGAT GATGTGGATT AATTCGATGC       60

AACGNGNAAA ACNTTACNTA CCCTNGACAT GTCTGGAACC TTGNTGNGAG GCGAGGGTGC      120

CTTCGGGAGC CAGAACACAG GTGCTGCATG GCTGTCGTCA GCTCGTGTCG TGAGATGNTG      180

GGTTAAGTCC CGCAACGAGC GCAACCCTTG TCAATAGTTG CCATCATTTG GTTGGGCACT      240

CTAGTGAGAC TGCCGGTGAC AAACCGGAGG AAGGTGGGGA TGACGTCAAG TCCTCATGGC      300

CCTTATGGGT AGGGCTTCAC ACGTCATACA ATGGTCGGTA CAGAGGGTTG CCAAGCCGCG      360

AGGTGGAGCC AATCCCTTAA AGCCGATCGT AGTCCGGATC GTAGTCTGCA ACTCGACTAC      420

GTGAAGTCGG AATCGGTAGT AATCGCAGAT CAGCATGCTG CGGTGAATAC GTTCCCGGGT      480

CTTGTACACA CCGCCCGTCA CACCATGGGA GTGGGTTTCA CCAGAAGTAG GTAGCTTAAC      540

CTTCGGGGAG GGCGCTTACC ACGGTGAGAT TNCATGACT                             579

(2) INFORMATION FOR SEQ ID NO:4:

(i) SEQUENCE CHARACTERISTICS:

(A) LENGTH: 408 base pairs
        (B) TYPE: nucleic acid
        (C) STRANDEDNESS: single
        (D) TOPOLOGY: linear (xi) SEQUENCE DESCRIPTION: SEQ ID NO:4:

ATGTTGGGGT TAAGTCCCGC AAACGAGCGC AAACCTTGTC ACTAGTTGCC ATCATTTGGT        60

TGGGCAATTC TAGTGAGACT GCCGGTGACA AACCGGAGGA AGGTGGGGAT GACGTCAAGT       120

CCTCATGGCC CTTATGGGTA GGGCTTCAAC AACGTCATAC AATGGTCGGT ACAGAGGGTT       180

GCCAAGCCGC GAGGTGGAGC CAATCCCTTG AAGCCGATCG TAGTCCGGAT CGTAGTCTGC       240

AACTCGACTA CGTGAAGTCG GAATCGCTAG TAATCGCAGA TCAGCATGCT GCGGTGAATA       300

CGTTCCCGGG TCTTGTACAC ACCGCCCGTC ACACCATGGG AGTGGGTTTC ACCAGAAGTA       360

GGTAGCTTAA CCTTCGGGAG GGCGCTTACC ACGGTGAGAT TCATGACT                    408

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:5:

TCTGCCGTAC TCTAGCCTT                                                     19

(2) INFORMATION FOR SEQ ID NO:6:

(i) SEQUENCE CHARACTERISTICS:
        (A) LENGTH: 1396 base pairs
        (B) TYPE: nucleic acid
        (C) STRANDEDNESS: single
        (D) TOPOLOGY: linear (xi) SEQUENCE DESCRIPTION: SEQ ID NO:6:

AGAGTTTGAT CATGGCTCAG AACGAACGCT GGCGGCAGGC CTAACACATG CAAGTCGAAC        60

GCCCCGCAAG GGGAGTGGCA GACGGGTGAG TAACACGTGG GAACCTTCCC TATAGTACGG       120

AATAGCCCAG GGAAACTTG GAGTAATACC GTATACGCCC GAAAGGGGAA AGAATTTCGC        180

TATAGGATGG GCCCGCGTAG GATTAGCTAG TTGGTGAGGT AATGGCTCAC CAAGGCGACG       240

ATCCTTAGCT GGTTTGAGAG AACGACCAGC CACACTGGGA CTGAGACACG GCCCAGACT        300

CCTACGGGGA GGCAGCAGTG GGGAATATTG GACAATGGGC GCAAGCCTGA TCAGCCATGC       360

CGCGTGAGTG ATGAAGGCTT AAGGGTTGTA AAGNTTTTTG GCGGGGGACG ATSSTGACGG       420

TAACCCGCAG AATAAGTCCC GGCTAAATTC GTGCCAGCAG CCGCGGTAAT ACGAAGGGGA       480

CTAGCGTTGT TCGGAATCAC TGGGCGTAAA GCGCACGTAG GCGGATATGC CAGTCAGTCC       540

GATAGAGGTG GGTGGAATTC CTAGTGTAGA GGTGAAATTC GTAGATATTA CGAAGAACAC       600

CGGTGGCGAA GGCGGCCCAC TGGATCGGTA CTGACGCTGA GGTGCGAAAG CGTGGGGAGC       660

AAACAGGATT AGATACCCTG GTAGTCCACG CCGTAAACGA TGGATGCTAG CCGTCGGATA       720

GCTTGCTATT CGGTGGCGCA GCTAACGCAT TAAGCATCCC GCCTGGGGAG TTACGGCCGC       780

AAGGTTAAAA CTCAAAGGAA TTGACGGGGG CCCGCACAAG CGGTGGAGCA TGTGGTTTAA       840

TTCGACGCAA CGCGAAGAAA CTTACCAGCT CTTGACATTC ACTGATTGCC GGTANAGATG       900

CCGGAGTTCC AGCAATGGAC AGTGGGACAG GTGCTGCATG GCTGTCGTCA GCTCGTGTCG       960

TGAGATGTTG GGTTAAGTCC CGCAACGAGC GCAACCCTCG CCATTAGTTG CCATCATTCA      1020

```
GTTGGGCACT CTAGTGGGAC TGCCGGTGAT AAGCCGGAGG AAGGTGGGGA TGACGTCAAG    1080

TCATCATGGC CCTTACGGGC TGAGCTACAC ACGTTGCTAC AATGGCGGTG ACAATGCGCA    1140

GCCACCTAGT AATAGGGGC TAATCGCAAA AAGCCGTCTC AGTTCAGATT GAGGGTCTGC     1200

AACTCGACCT CATGAAGTCG GAATCGCTAG TAATCGCGCA TCAGCATGGC GCGGTGAATA    1260

CGTTCCCGGG CCTTGTACAC ACCGCCCGTC ACACCATGGG AGTTGGTCTT ACCCTAAAAC    1320

GGTGCGCTAA CCGCAAGGAG GCAGCCGGCC ACGGTAAGGT CAGCGACTGG GGTGAAGTCG    1380

TAACAAGGTA ACCGTA                                                    1396

(2) INFORMATION FOR SEQ ID NO:7:

(i) SEQUENCE CHARACTERISTICS:
        (A) LENGTH: 1483 base pairs
        (B) TYPE: nucleic acid
        (C) STRANDEDNESS: single
        (D) TOPOLOGY: linear (xi) SEQUENCE DESCRIPTION: SEQ ID NO:7:

CAGTGTGATG GATATCTGCA GAATTCGGCT TTTTGATCAT GGCTCAGAAC GAACGCTGGC      60

GGCAGGCCTA ACACATGCAA GTCGAACGCC CCGCAAGGGG AGTGGCAGAC GGGTGAGTAA     120

CACGTGGGAA CCTTCCCTAT AGTACGGAAT AGCCCAGGGN AAACTTGGAG TAATACCGTA    180

TACGCCCGAA AGGGGAAAGA ATTTCGCTAT AGGATGGGCC CGCGTAGGAT TAGCTAGTTG    240

GTGAGGTAAT GGCTCACCAA GGCGACGATC CTTAGCTGGT TTGAGAGAAC GACCAGCCAC    300

ACTGGGACTG AGACACGGCC CCAACTCCTA CGGGAGGCAG CNAGTGGGGA ATATTGGAAC    360

AATGGGCGC AAAGCCTGAA TCCACCATGC GGCGTGAGTG ATGAAGGCTT AGGGGTTGTA     420

AAGNTTTTTG GCGGGACGA TAATGACGGT AACCGHCAGA ATAAGTCCCG GCTAAATTTC     480

GTGCCAGCAG CCGCGGTAAT ACGGAAGGGA TAGCGTTGTT CGGAATCACT GGGCGTAAAG    540

CGCACGTAGG CGGATATGCC AGTCAGGGGT GAAATCCCGG GGCTCAACCT CGGAACTGCC    600

CTTGATACAG CATGTCTTGA GTCCGATAGA GGTGGGTGGA ATTCCTAGTG TAGAGGTGAA    660

ATTCGTAGAT ATTAGGAAGA ACACCGGTGG CGAAGGCGGC CCACTGGATC GGTACTGACG    720

CTGAGGTGCG AAAGCGTGGG GAGCAAACAG GATTAGATAC CCTGGTAGTC CACGCCGTAA    780

ACGATGGATG CTAGCCGTCG GATAGCTTGC TATTCGGTGG CGCAGCTAAC GCATTAAGCA    840

TCCCGCCTGG GGAGTTACGG CCGCAAGGTT AAAACTCAAA GGAATTGACG GGGCCCGGC    900

NGCACAAGCG GTGGAGCATG TGGTTTAATT CGACGCAACG CGAAGAACCT TACCAGCTCT    960

TGACATTCAC TGATTGCCGG TANAGATGCC GGAGTTCCAG CAATGGACAG TGGGACAGGT    1020

GCTGCATGGC TGTCGTCAGC TCGTGTCGTG AGATGTTGGG TTAAGTCCCG CAACGAGCGC    1080

AACCCTCGCC ATTAGTTGCC ATCATTCAGT TGGGCACTCT AGTGGGACTG CCGGTGATAA    1140

GCCGGAGGAA GGTGGGGATG ACGTCAAGTC ATCATGGCCC TTACGGGCTG GCTACACAC    1200

GTTGCTACAA TGGCGGTGAC AATGCGCAGC CAACCTAGTA ATAGGGAGCT AATCGCAAAA    1260

AGCCGTCTCA GTTCAGATTG AGGTCTGCAA CTCGACCTCA TGAAGTCGAA TCGCTAGTAA    1320

TCGCGCATCA GCATGGCGCG GTGAATACGT TCCCGGGCCT TGTACACACC GCCCGTCACA    1380

CCATGGGAGT TGGTCTTACC CTAAAACGGT GCGCTAACCG CAAGGAGGCA GCCGGCCACG    1440

GTAAGGTCAG CGACTGGGGT GAAGTCGTAA CAAGGTAGCC GTA                      1483

(2) INFORMATION FOR SEQ ID NO:8:

(i) SEQUENCE CHARACTERISTICS:
```

(A) LENGTH: 396 base pairs
                (B) TYPE: nucleic acid
                (C) STRANDEDNESS: single
                (D) TOPOLOGY: linear (xi) SEQUENCE DESCRIPTION: SEQ ID NO:8:

```
ATGTTGGGTT AAGTCCCGCA ACGAGCGCAA CCCTCGCCAT TAGTTGCCAT CATTAAGTYG      60

GGCACTCTAG TGGGAMTGCC GGTGATAAGC CGGAGGAAGG TGGRGATGAC GTCAAGTCAT     120

CATGGCCCTT ATGGGSTGGG ATACACACGT GGTACAATGG CGGTGACAAT GGGCAGCGAG     180

GCGGSAATGC CRAGCTAATC TCAAAAAGCC GTCTCAGTTS GGATTGGGCT CTGCAAGTCG     240

AGCCCATGAA GTNGGAATCG GTAGTAATCG TGGATCAGCA CGCCACGNTG AATACGTTCC     300

CGGGCCTTGT ACACACCGCC CGTCACACCA TGGGAGTTGG CTTTACCCGA AGACGGTGCG     360

CTAACCAGCA ATGGAGGCAG CCGGCCACGG TAAGTC                              396
```

(2) INFORMATION FOR SEQ ID NO:9:

(i) SEQUENCE CHARACTERISTICS:
                (A) LENGTH: 402 base pairs
                (B) TYPE: nucleic acid
                (C) STRANDEDNESS: single
                (D) TOPOLOGY: linear (xi) SEQUENCE DESCRIPTION: SEQ ID NO:9:

```
ATGTTGGGTT AAGTCCCGCA ACGAGCGCAA CCSTCGCCAT TAGTTGCCAT CATTAAGTTG      60

GGCACTCTAG TGGGACTGCC GGTGATAAGC CGGAGGAAGG TGGGGATGAC GTCAAGTCAT     120

CATGGCCCTT ATGGGCTGGG VTACACACGT GSTACAATGG CGGTGACAAT GGGCAGCGAG     180

GCAGCAATGC CAAGCTAATC TCAAAAAGCC GTCTCAGTTC GGATTGGGCT CTGCAACTCG     240

AGCCCATGAA GTCGGAATCG CTAGTAATCG TGGATCAGCA CGCCACGGTG AATACGTTCC     300

CGGGCCTTGT ACACACCGCC CGTCACACCA TGGGAGTTGG CTTTACCCGA AGACGGTGCG     360

CTAACCAGCA ATGGAGGCAG CCGGCCACGG TAAGTCGAGC GA                       402
```

(2) INFORMATION FOR SEQ ID NO:10:

(i) SEQUENCE CHARACTERISTICS:
                (A) LENGTH: 405 base pairs
                (B) TYPE: nucleic acid
                (C) STRANDEDNESS: single
                (D) TOPOLOGY: linear (xi) SEQUENCE DESCRIPTION: SEQ ID NO:10:

```
ATGTTGGGTT AAGTCCCGCA ACGAGCGCAA CCCTCGCCAT TAGTTGCCAT CATTCAGTTG      60

GGCACTCTAG TGGGACTGCC GGTGATAAGC CGGAGGAAGG TGGGGATGAC GTCAAGTCAT     120

CATGGCCCTT ACGGGCTGGG CTACACACGT GCTACAATGG CGGTGACAAT GCGCAGCCAC     180

CTAGCAATAG GGAGCTAATC GCAAAAAGCC GTCTCAGTTC AGATTGGAGT CTGCAACTCG     240

ACTCCATGAA GTCGGAATCG CTAGTAATCG CGCATCAGCA TGGCGCGGTG AATACGTTCC     300

CGGGCCTTGT ACACACCGCC CGTCACACCA TGGGAGTTGG TCATACCCTA AAACGGTGCG     360

CTAACCGCAA GGAGGCAGCC GGCCACGGTA TGTCCAGCGA CTGGG                    405
```

(2) INFORMATION FOR SEQ ID NO:11:

(i) SEQUENCE CHARACTERISTICS:
                (A) LENGTH: 405 base pairs
                (B) TYPE: nucleic acid
                (C) STRANDEDNESS: single
                (D) TOPOLOGY: linear (xi) SEQUENCE DESCRIPTION: SEQ ID NO:11:

```
ATGTTGGGTT AAGTCCCGCA ACGAGCGCAA CCCTCGCCAT TAGTTGCCAT CATTCAGTTG      60
GGCACTCTAG TGGGACTGCC GGTGATAAGC CGGAGGAAGG TGGGGATGAC GTCAAGTCAT     120
CATGGCCCTT ACGGGCTGGG CTACACACGT GCTACAATGG CGGTGACAAT GCGCAGCCAC     180
CTAGCAATAG GGAGCTAATC GCAAAAAGCC GTCTCAGTTC AGATTGGAGT CTGCAACTCG     240
ACTCCATGAA GTCGGAATCG CTAGTAATCG CGCATCAGCA TGGCGCGGTG AATACGTTCC     300
CGGGCCTTGT ACACACCGCC CGTCACACCA TGGGAGTTGG TCATACCCTA AAACGGTGCG     360
CTAACCGCAA GGAGGCAGCC GGCCACGGTA TGTCNAGCGA CTGGG                    405
```

(2) INFORMATION FOR SEQ ID NO:12:

(i) SEQUENCE CHARACTERISTICS:
        (A) LENGTH: 407 base pairs
        (B) TYPE: nucleic acid
        (C) STRANDEDNESS: single
        (D) TOPOLOGY: linear (xi) SEQUENCE DESCRIPTION: SEQ ID NO:12:

```
ATGTTGGGTT AAGTCCCGCA ACGAGCGCAA CCCTCGCCAT TAGTTGCCAT CATTTAGTTG      60
GGCACTCTAG TGGGACTGCC GGTGATAAGC CGGAGGAAGG TGGGGATGAC GTCAAGTCAT     120
CATGGCCCTT ACGGGCTGGG CTACACACGT GCTACAATGG CGGTGACAAT GCGCAGCCAC     180
CTAGCAATAG GGAGCTAATC GCAAAAAGCC GTCTCAGTTC AGATTGGAGT CTGCAACTCG     240
ACTCCATGAA GTCGGAATCG CTAGTAATCG CGCATCAGCA TGGCGCGGTG AATACGTTCC     300
CGGGCCTTGT ACACACCGCC CGTCACACCA TGGGAGTTGG TTTTACCCGA AGACGGTGCG     360
CTAACCCGCA AGGGAGGCAG CCGGCCACGG TAAGTCCAGC GACTGGG                  407
```

(2) INFORMATION FOR SEQ ID NO:13:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (xi) SEQUENCE DESCRIPTION: SEQ ID NO:13:

```
ATGTTGGGTT AAGTCCCGCA ACGAGCGCAA CCCTCGCCAT CAGTTGCCAT CATTAAGTTG      60
GGCACTCTGG TGGGACTGCC GGTGATAAGC CGGAGGAAGG TGGGGATGAC GTCAAGTCAT     120
CATGGCCCTT ACGGGCTGGG CTACACACGT GTTACAATGG CGGTGACAAT GCGCAGCCAC     180
CTCGCGAGAG GGAGCTAATC GCAAAAAGCC GTCTCAGTTC GGATTGGGCT CTGCAACTCG     240
AGCCCATGAA GTTGGAATCG YTAGTAATCG CGCATCAGCA TGGCGCGGTG AATACGTTCC     300
CGGGCCTTGT ACACACCGCC CGTCACACCA TGGGAGTTGG CTTTACCCGA AGGCGGTGCG     360
CTAACCGCAA GGAGGCAGCC GGCCACGGTA AGTCAGCGA                           399
```

(2) INFORMATION FOR SEQ ID NO:14:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (xi) SEQUENCE DESCRIPTION: SEQ ID NO:14:

```
ATGTTGGGTT AAGTCCCGCA ACGAGCGCAA CCCTCGCCAT TAGTTGCCAT CATTCAGTTG      60
```

```
GGCACTCTAG TGGGACTGCC GGTGATAAGC CGGAGGAAGG TGGGGATGAC GTCAAGTCAT      120

CATGGCCCTT ATGGGCTGGG ATACACACGT GCTACAATGG CGGTGACAAT GCGCAGCCAC      180

TCAGCAATGA GGAGCTAATC GCAAAAAGCC GTCTCAGTTC GGATTGGGGT CTGCAACTCG      240

ACCCCATGAA GTCGGAATCG CTAGTAATCG CGCATCAGCA CGGCGCGGTG AATACGTTCC      300

CGGGCMTTGT ACACACCGCC CGTCACACCA TGGGAGTTGG CTTTACCCGA AGGTAGTGCG      360

CTAACCGCAA GGAGGCAGCT AACCACGGTA AGTCAG                                396

(2) INFORMATION FOR SEQ ID NO:15:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (xi) SEQUENCE DESCRIPTION: SEQ ID NO:15:

ATGTTGGGTT AAGTCCCGCA ACGAGCGCAA CCCTCGCCAT TAGTTGCCAT CATTCAGTTG       60

GGCACTCTAG TGGGACTGCC GGTGATAAGC CGGAGGAAGG TGGGGATGAC GTCAAGTCAT      120

CATGGCCCTT ACGGGCTGGG CTACACACGT TGCTACAATG GCGGTGACAA TGCGCAGCCA      180

ACCTAGTAAT AGGGAGCTAA TCGCAAAAAG CCGTCTCAGT TCAGATTGAG GTCTGCAACT      240

CGACCTCATG AAGTCGAATC GCTAGTAATC GCGCATCAGC ATGGCGCGGT GAATACGTTC      300

CCGGGCCTTG TACACACCGC CCGTCACACC ATGGGAGTTG GTCTTACCCT AAAACGGTGC      360

GCTAACCGCA AGGAGGCAGC CGGCCACGGT AAGGTCAGCG ACTGGGGTGA AGTCGTAACA      420

AGGTAGCCGT A                                                          431

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:16:

GCTGCCCATT GTCACCGCC                                                   19

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:17:

GCTGCGCATT GTCACCGCC                                                   19

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:18:

CTGCCCGTAC TCTAGTTAT                                                   19
```

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:19:

```
TGCCAAACTC TAGCCTTG                                          18
```

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

```
GCTGCCTCCC GTAGGAGT                                          18
```

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:21:

```
AGAGTTTGAT CMTGGCTCAG                                        20
```

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:22:

```
TACGGYTACC TTGTTACGAC T                                      21
```

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE: M = C/A (xi) SEQUENCE DESCRIPTION: SEQ ID NO:23:

```
AGAGTTTGAT CMTGGCTCAG                                        20
```

(2) INFORMATION FOR SEQ ID NO:24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE: K = G/T (xi) SEQUENCE DESCRIPTION: SEQ ID NO:24:

ACGVGTTACK CACCCGT                                                          17

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE: K = G/T; R = A/G (xi) SEQUENCE DESCRIPTION: SEQ ID NO:25:

AKRCATTACTC ACCCGT                                                          17

(2) INFORMATION FOR SEQ ID NO:26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE: Y = C/T (xi) SEQUENCE DESCRIPTION: SEQ ID NO:26:

CTGCTGCSYC CCGTAG                                                           16

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:27:

CTCCTACGGG AGGCAGCAG                                                        19

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE: W = A/T; K = G/T (xi) SEQUENCE DESCRIPTION: SEQ ID NO:28:

GWATTACCGC GGCKGCTG                                                         18

(2) INFORMATION FOR SEQ ID NO:29:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE: M = C/A (xi) SEQUENCE DESCRIPTION: SEQ ID NO:29:

GTGCCAGCMG CCGCGG                                                           16

(2) INFORMATION FOR SEQ ID NO:30:

```
   (i) SEQUENCE CHARACTERISTICS:
       (A) LENGTH: 20 base pairs
       (B) TYPE: nucleic acid
       (C) STRANDEDNESS: single
       (D) TOPOLOGY: linear (ix) FEATURE: R = A/G; Y = C/T (xi) SEQUENCE DESCRIPTION: SEQ ID NO:30:

TCTACGRATT TCACCYCTAC                                                  20

(2) INFORMATION FOR SEQ ID NO:31:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ix) FEATURE:Y = C/T (xi) SEQUENCE DESCRIPTION: SEQ ID NO:31:

TCTACGCATT TCACYGCTAC                                                  20

(2) INFORMATION FOR SEQ ID NO:32:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ix) FEATURE:Y = C/T (xi) SEQUENCE DESCRIPTION: SEQ ID NO:32:

TCTRCGCTTY CACCGCTAC                                                   19

(2) INFORMATION FOR SEQ ID NO:33:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ix) FEATURE:M = C/A; R = A/G (xi) SEQUENCE DESCRIPTION: SEQ ID NO:33:

CCGTCAATTC MTTRAGTTT                                                   19

(2) INFORMATION FOR SEQ ID NO:34:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ix) FEATURE:Y = C/T; K = G/T (xi) SEQUENCE DESCRIPTION: SEQ ID NO:34:

AAACTYAAAK GAATTGACGG                                                  20

(2) INFORMATION FOR SEQ ID NO:35:

(i) SEQUENCE CHARACTERISTICS:
       (A) LENGTH: 15 base pairs
       (B) TYPE: nucleic acid
       (C) STRANDEDNESS: single
```

(D) TOPOLOGY: linear (xi) SEQUENCE DESCRIPTION: SEQ ID NO:35:

GGGTTGCGCT CGTTG                                                        15

(2) INFORMATION FOR SEQ ID NO:36:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (xi) SEQUENCE DESCRIPTION: SEQ ID NO:36:

GCAACGAGCG CAACCC                                                       16

(2) INFORMATION FOR SEQ ID NO:37:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ix) FEATURE:R = A/G (xi) SEQUENCE DESCRIPTION: SEQ ID NO:37:

ACGGGCGGTG TGTRC                                                        15

(2) INFORMATION FOR SEQ ID NO:38:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ix) FEATURE:Y = C/T (xi) SEQUENCE DESCRIPTION: SEQ ID NO:38:

TGYACACACC TCCCGT                                                       16

(2) INFORMATION FOR SEQ ID NO:39:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ix) FEATURE:Y = C/T (xi) SEQUENCE DESCRIPTION: SEQ ID NO:39:

TACGGYTACC TTGTTACGAC TT                                                22

(2) INFORMATION FOR SEQ ID NO:40:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ix) FEATURE:W = A/T; R = A/G (xi) SEQUENCE DESCRIPTION: SEQ ID NO:40:

AAGGAGGTGW TCCARCC                                                      17

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:41:

GTTTTCCCAG TCACGAC                              17

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:42:

CAGGAAACAG CTATGAC                              17